(12) United States Patent
Rock

(10) Patent No.: US 9,357,238 B2
(45) Date of Patent: May 31, 2016

(54) VIDEO DATA EXTENSION SYSTEM AND METHOD

(71) Applicant: Eric Lee Rock, Plano, TX (US)

(72) Inventor: Eric Lee Rock, Plano, TX (US)

( * ) Notice: Subject to any disclaimer, the term of this patent is extended or adjusted under 35 U.S.C. 154(b) by 0 days.

(21) Appl. No.: 14/223,652

(22) Filed: Mar. 24, 2014

(65) Prior Publication Data
US 2014/0297328 A1    Oct. 2, 2014

Related U.S. Application Data

(63) Continuation-in-part of application No. 14/223,537, filed on Mar. 24, 2014.

(60) Provisional application No. 61/805,355, filed on Mar. 26, 2013.

(51) Int. Cl.
*H04N 5/445* (2011.01)
*G06Q 50/24* (2012.01)
(Continued)

(52) U.S. Cl.
CPC ........ *H04N 21/2143* (2013.01); *G06F 19/3418* (2013.01); *H04N 21/254* (2013.01); *H04N 21/4122* (2013.01); *H04N 21/4126* (2013.01); *H04N 21/4316* (2013.01); *H04N 21/4622* (2013.01)

(58) Field of Classification Search
CPC ................. G02B 2027/014; G02B 2027/0178; G06Q 50/24; G06Q 30/02; G06F 1/163; G06F 3/013; G06F 3/017; A61B 3/113; H04N 13/0468
USPC .......................................................... 705/2
See application file for complete search history.

(56) References Cited

U.S. PATENT DOCUMENTS

| 7,739,126 B1 | 6/2010 | Cave et al. |
| 8,183,998 B2 | 5/2012 | Rao et al. |

(Continued)

FOREIGN PATENT DOCUMENTS

WO    WO 2013033655 A1    3/2013

OTHER PUBLICATIONS

Charalampos Doukas, student Member IEEE, Thomas Pliakas, student Member IEEE and Ilias Maglogiannis, Member, IEEE, Mobile Healthcare Information Management utilizing Cloud computing and Android OS, Aug. 31-Sep. 4, 2010, 32nd Annual International conference of the IEEE EMBS Buenos Aires, Argentina.*

*Primary Examiner* — Hiep V Nguyen
(74) *Attorney, Agent, or Firm* — David W. Carstens; Kevin M. Klughart; Carstens & Cahoon, LLP

(57) ABSTRACT

A system and method extending mobile video data across multiple display hardware platforms is disclosed. The system incorporates a mobile user interface device (MUD) interacting with a video control unit (VCU) to present display video content (DVC) on a video display unit (VDU). The MUD and VCU coordinate to control their respective display content in real-time based on a specific integrated user interaction context (UIC) provided by the MUD to the VCU. The VCU executes the UIC to control the merging in real-time of primary video content (PVC) and secondary video content (SVC) that are combined to form the DVC. Video content processed by the VCU as PVC/SVC input may be sourced from external video sources (EVS) directly connected to the VCU and/or data sourced from a computer communications network (CCN) via routing through the MUD and/or VCU.

30 Claims, 16 Drawing Sheets

(51) Int. Cl.
*H04N 21/214* (2011.01)
*H04N 21/254* (2011.01)
*H04N 21/41* (2011.01)
*H04N 21/431* (2011.01)
*H04N 21/462* (2011.01)
*G06F 19/00* (2011.01)

(56) References Cited

U.S. PATENT DOCUMENTS

| | | | |
|---|---|---|---|
| 8,239,903 B1 * | 8/2012 | Campagna et al. | 725/107 |
| 8,301,233 B2 | 10/2012 | Zhang et al. | |
| 8,321,808 B2 | 11/2012 | Goetz et al. | |
| 8,326,651 B2 | 12/2012 | McLaren et al. | |
| 8,396,804 B1 | 3/2013 | Dala et al. | |
| 2002/0184055 A1 | 12/2002 | Naghavi et al. | |
| 2006/0234202 A1 | 10/2006 | Brown | |
| 2007/0191070 A1 * | 8/2007 | Rao | 455/566 |
| 2007/0255345 A1 | 11/2007 | Krause | |
| 2008/0242947 A1 | 10/2008 | Jung et al. | |
| 2008/0275317 A1 | 11/2008 | Cho et al. | |
| 2011/0029327 A1 | 2/2011 | Dunlop | |
| 2011/0166884 A1 | 7/2011 | Lesselroth et al. | |
| 2011/0234409 A1 | 9/2011 | Soliman | |
| 2011/0238435 A1 | 9/2011 | Rapaport et al. | |
| 2011/0295621 A1 | 12/2011 | Farooq et al. | |
| 2012/0041771 A1 | 2/2012 | Cosentino et al. | |
| 2013/0035955 A1 | 2/2013 | Torres | |
| 2013/0329058 A1 | 12/2013 | Brossette et al. | |

* cited by examiner

VIDEO DATA EXTENSION SYSTEM AND METHOD

U.S. PROVISIONAL PATENT APPLICATIONS

This application claims benefit under 35 U.S.C. §119 and incorporates by reference U.S. Provisional patent application for HEALTHCARE MANAGEMENT SYSTEM AND METHOD by inventor Eric Rock, filed electronically with the USPTO on Mar. 26, 2013, with Ser. No. 61/805,355, EFS ID 15358332, confirmation number 6386.

U.S. UTILITY PATENT APPLICATIONS

This application claims benefit under 35 U.S.C. §120 and incorporates by reference U.S. Utility patent application for HEALTHCARE DELIVERY SYSTEM AND METHOD by inventor Eric Rock, filed electronically with the USPTO on Mar. 24, 2014, with Ser. No. 14/223,537, EFS ID 18566745, confirmation number 2107. This patent application will be referred to herein as the HEALTHCARE DELIVERY SYSTEM AND METHOD patent application.

U.S. CONTINUATION-IN-PART (CIP) PATENT APPLICATION

This application is a continuation-in-part (CIP) patent application of and incorporates by reference U.S. Utility patent application for HEALTHCARE DELIVERY SYSTEM AND METHOD by inventor Eric Rock, filed electronically with the USPTO on Mar. 24, 2014, with Ser. No. 14/223,537, EFS ID 14223537, confirmation number 2107. This patent application will be referred to herein as the HEALTHCARE DELIVERY SYSTEM AND METHOD patent application.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for coordinating the display of a number of video data sources for presentation to a user on mobile and non-mobile devices. Without limiting the scope of the present invention, the present invention may be advantageously applied to healthcare delivery systems that incorporate mobile deployment of video content and medical instrumentation device integration for patient monitoring.

PRIOR ART AND BACKGROUND OF THE INVENTION

Prior Art System Context

Within the context of a mobile user device (MUD) such as computer tablets, smartphones, laptops, and the like there are often situations in which the screen displays of the MUD are insufficient to provide the desired screen resolution necessary to properly display content to a user. While many users also have access to a video display unit (VDU) such as a HDTV monitor or the like, there is often not a coordinated system or method to deploy content from the MUD to the VDU. Furthermore, for mobile software applications that are coordinated from a host computer system (HCS), there are often scenarios in which autonomous MUD operation without communication to the HCS is desirable. Often there is primary video content (PVC) that may be displayed on the VDU but which is incompatible with the viewing of secondary video content (SVC) that is provided by the HCS and/or the MUD. In these situations there is an unmet industry need to be able to coordinate the input/display environments associated with HCS/MUD and that of the VDU in a way that permits optimal use of these resources to enhance the overall user input/output experience with respect to interaction with the MUD and VDU.

Deficiencies in the Prior Art

The prior art as detailed above suffers from the following deficiencies:
- Prior art video data extension systems and methods do not permit integration of mobile video content across the VDU and the MUD.
- Prior art video data extension systems and methods do not permit real-time merging of MUD SVC and PVC material on the VDU.
- Prior art video data extension systems and methods do not permit prioritization of PVC and SVC material.
- Prior art video data extension systems and methods do not integrate the use of a remote control unit (RCU) with MUD user input interactions.
- Prior art video data extension systems and methods do not permit coordination of MUD/VDU input/output under direction of dynamic mobile video content (MVC) control.
- Prior art video data extension systems and methods are unable to integrate the execution of patient healthcare plans (PHPs) that operate autonomously on the MUD.

While some of the prior art may teach some solutions to several of these problems, the core issue of integrating the user experience between the MUD and VDU has not been solved by the prior art.

OBJECTIVES OF THE INVENTION

Accordingly, the objectives of the present invention are (among others) to circumvent the deficiencies in the prior art and affect the following objectives in the context of a video data extension system and method:
(1) Provide for a video data extension system and method that permits integration of mobile video content across the VDU and the MUD.

(2) Provide for a video data extension system and method that permits real-time merging of MUD SVC and PVC material on the VDU.
(3) Provide for a video data extension system and method that permits prioritization of PVC and SVC material.
(4) Provide for a video data extension system and method that integrates the use of a remote control unit (RCU) with MUD user input interactions.
(5) Provide for a video data extension system and method that permits coordination of MUD/VDU input/output under direction of dynamic mobile video content (MVC) control.
(6) Provide for a video data extension system and method that is able to integrate video content with the execution of patient healthcare plans (PHPs) that operate autonomously on the MUD.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention as embodied in a system and method utilizes a number of interconnected computers to affect the following coordination of video display content:
  A mobile user device (MUD) retrieves mobile video content (MVC) from a host computer system (HSC) via a computer communication network (CCN).
  The MUD transmits the MVC to a video control unit (VCU) via a wireless communication link (WCL).
  The VCU accepts primary video content (PVC) from an external video source (EVS).
  The VCU is accepts the MVC as secondary video content (SVC) from the MUD.
  The VCU is configured to transmit display video context (DVC) to a video display unit (VDU) for presentation to a user.
  The MUD is configured to define a user interaction context (UIC) that controls integration of the PVC and the SVC on the VCU in real-time.
  The UIC is selected from one of a variety of operational modes that define the interaction between the user, the MUD, and the VDU.
  The MUD transmits the UIC to the VCU via the WCL.
  The VCU is configured to execute the UIC to generate a display video context (DVC) from the PVC and the SVC.

This system may be combined with a video data extension method used to affect integration of a variety of video sources for simultaneous albeit disparate display on a number of different video hardware displays.

BRIEF DESCRIPTION OF THE DRAWINGS

For a fuller understanding of the advantages provided by the invention, reference should be made to the following detailed description together with the accompanying drawings wherein.

DESCRIPTION OF THE PRESENTLY PREFERRED EXEMPLARY EMBODIMENTS

Figure 1:
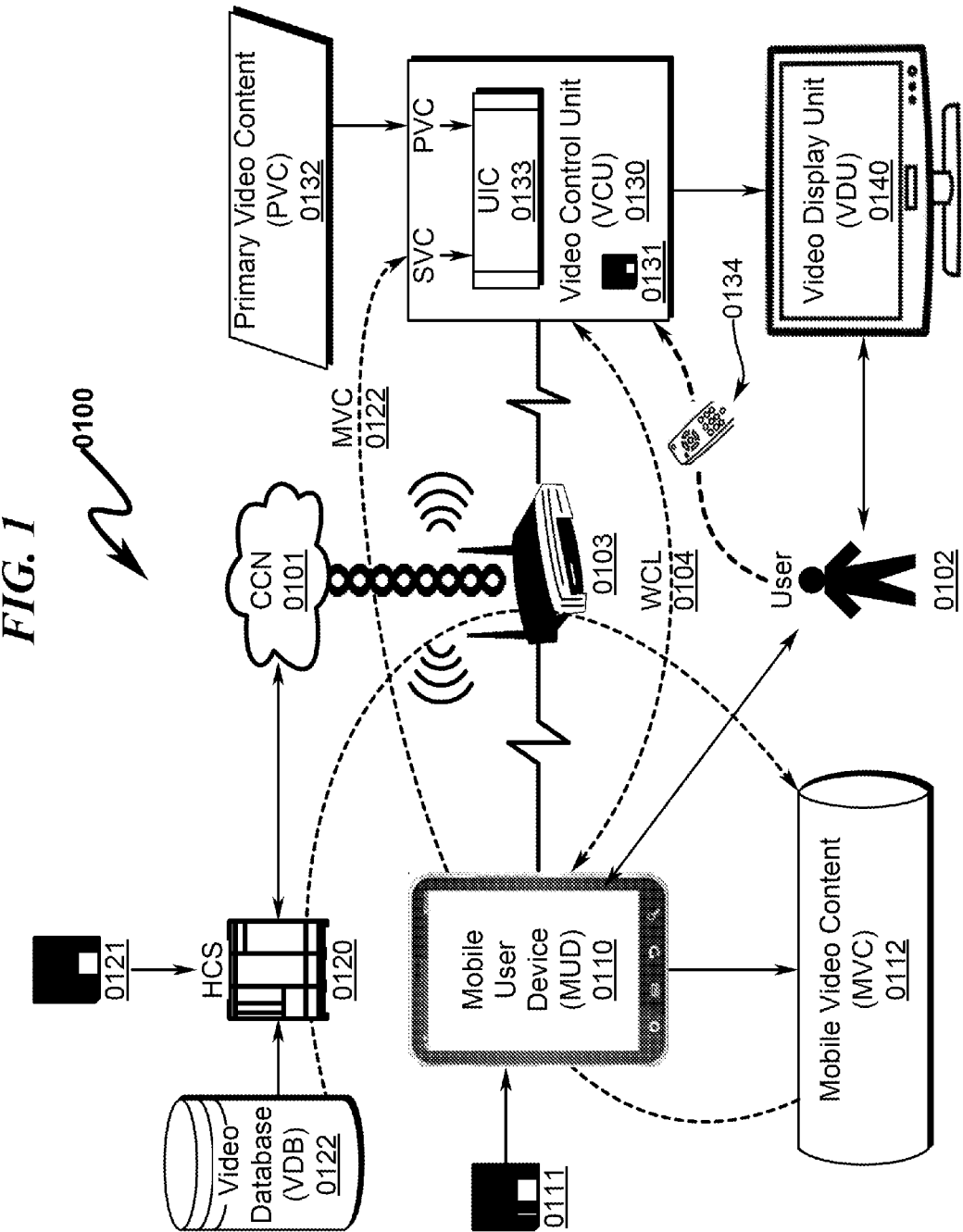
FIG. 1 illustrates an exemplary video data extension system context.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a VIDEO DATA EXTENSION SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Primary/Secondary Video Content not Limitive

Within the description of the present invention provided herein the terms primary video content (PVC) and secondary video content (SVC) are provided as arbitrary designators for video data content provided to the video control unit (VCU) and should not be considered limitive of the VCU functionality. In some circumstances the designations of these ports may be swapped while in other circumstances the VCU may be configured with more than two video input ports that are utilized for video input switching.

System Overview (0100)

The present invention may be summarized as depicted in the system block diagram of FIG. 1 (0100), and is comprised of three cooperating computer systems as depicted by the mobile user device (0110), host computer system (HCS) (0120), and video control unit (VCU) (0130). Each of these computer systems operates under control of machine instructions read from computer readable medium (0111, 0121, 0131). Within this context the system operates to coordinate the integration of primary video content (PVC) (0132) (that may be sourced from a variety of sources such as over-the-air TV broadcasts, Internet broadcasts, MPEG videos, streaming video content, and the like) and video content from the HCS (0120) (typically retrieved from a video database (VDB) (0122) over a computer communication network (CCN) (0101) (such as the Internet)) to produce a display video context (DVC) that is then transmitted to a video control unit (VCU) (0130) for presentation to a user (0102) on a video display unit (VDU) (0140).

The HCS (0120) video content derived from the VDB (0122) may also be stored locally to the MUD (0110) as mobile video content (MVC) (0112) and streamed to the VCU (0130) by the MUD (0110) directly as secondary video content (SVC) that is merged with primary video content (PVC) (0132) to form the DVC that is then transmitted to a video control unit (VCU) (0130). How the PVC and SVC are merged by the VCU (0130) to form the DVC is determined by a user interaction context (UIC) (0133) that is defined by the MUD (0110) and transmitted to the VCU (0130) for real-time execution of the PVC/SVC merging process to form the DVC VDU (0140) video content. Within this context the VCU (0130) may be controlled by autonomous user interaction scripts (that may include a patient healthcare plan (PHP) as described in the patent application HEALTHCARE DELIVERY SYSTEM AND METHOD incorporated herein) running on the MUD (0110) that control the UIC executed on the VCU (0130). The use of a remote control unit (RCU) (0134) as a user (0102) interaction device is also anticipated in this application context.

Method Overview (0200)

Figure 2:
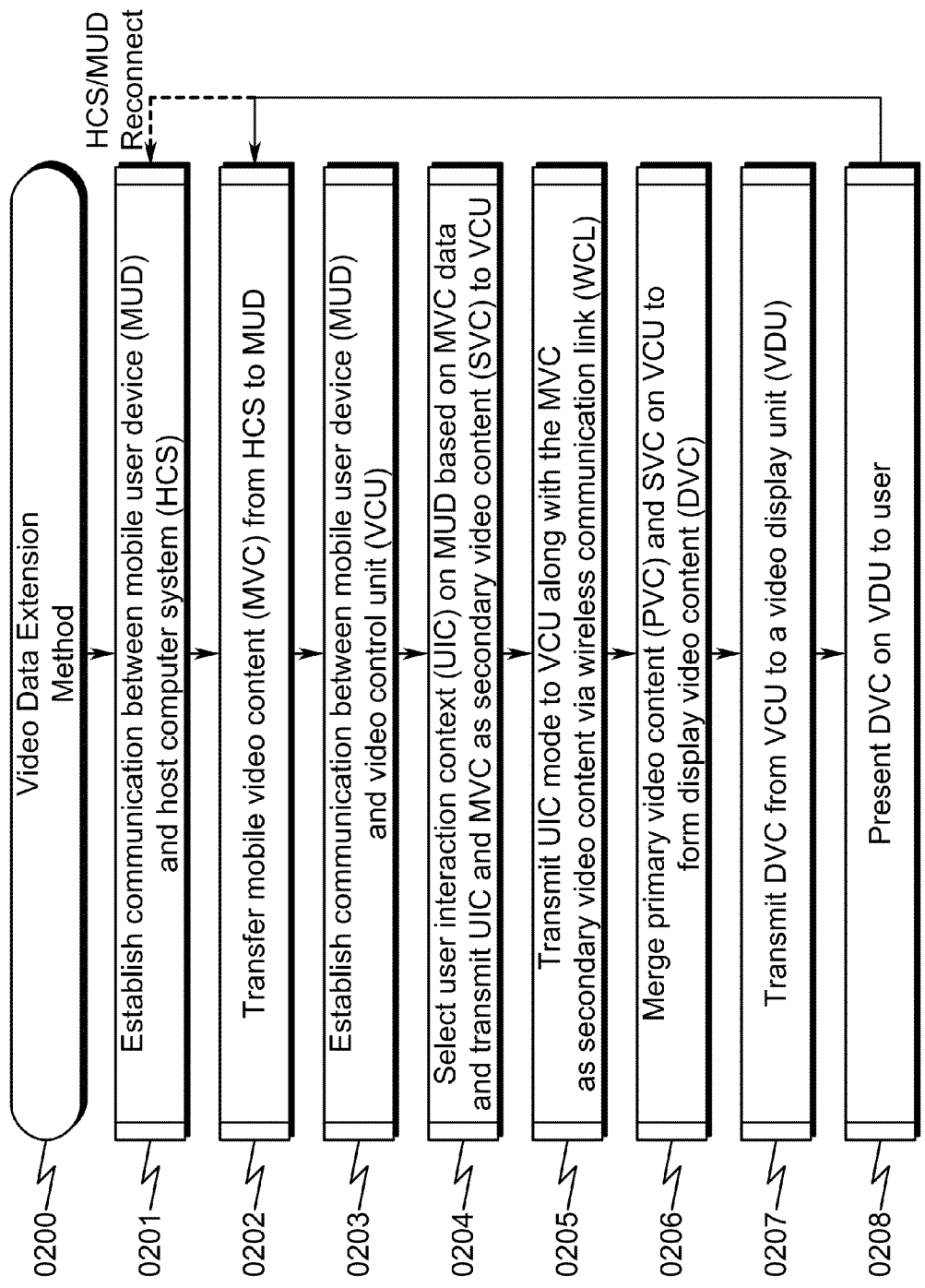
FIG. 2 illustrates an exemplary video data extension method.

The system context as depicted in FIG. 1 (0100) is typically associated with a methodology as depicted in FIG. 2 (0200) and involves the following steps:
(1) Communication is established between the mobile user device (MUD) and the host computer system (HCS) (0201);
(2) Mobile video content (MVC) is transferred between the HCS to the MUD (0202);
(3) Communication is established between the MUD and a video control unit (VCU) (0203);
(4) A user interaction context (UIC) is selected by the MUD based on the MVC data (0204);
(5) The MUD transmits the UIC along with the MVC data as secondary video content (SVC) to the VCU using a wireless communication link (WCL) (0205);
(6) The VCU merges the PVC and SVC in real-time to form display video content (DVC) based on the UIC (0206);
(7) The VCU transmits the DVC to the VDU (0207); and
(8) The DVC is presented to the user on the VDU (0208) and the process proceeds either to step (2) or step (1) depending on the HCS/MUD communication link status.

Note that both the UIC execution by the VCU and the potential UIC selection by the MUD may occur in real-time.

Healthcare System Embodiment Overview (0300)

Figure 3:
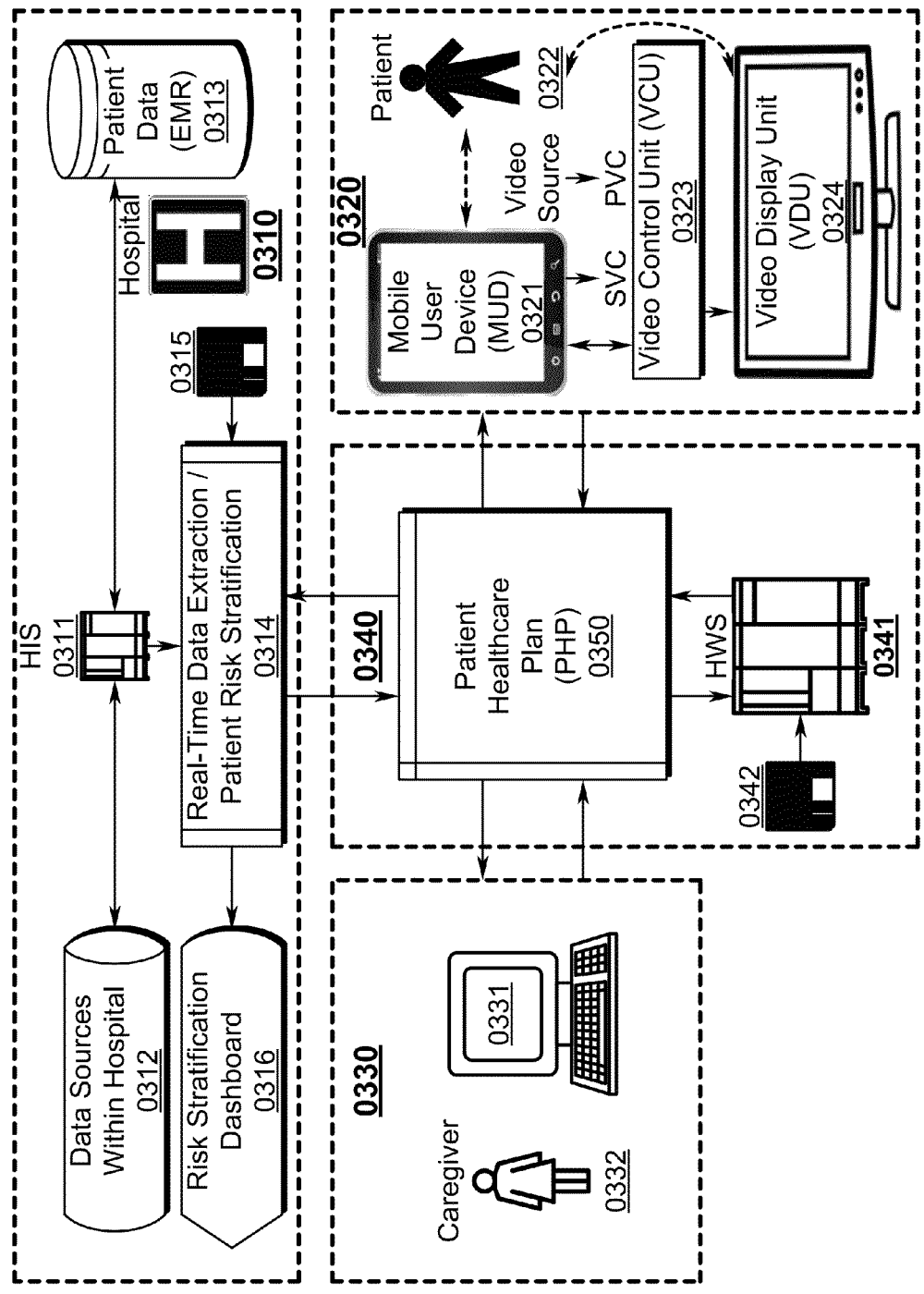
FIG. 3 illustrates a preferred exemplary overview block diagram of a preferred exemplary system embodiment of the present invention.

The present invention as applied to a healthcare system application context may be summarized as depicted in the system block diagram of FIG. 3 (0300), and is comprised of four cooperating computer systems as depicted by the HIS system (0310), patient remote monitoring system (0320), caregiver computer system(s) (0330), and healthcare web server (HWS) (0340) (also termed a host computer system (HCS) in this application). Within this context the system operates to integrate information from the various computer systems (0311, 0321, 0331, 0341) as dictated by an overarching patient healthcare plan (PHP) (0350) executed as machine instructions read from a computer readable medium (0342) that drives information flow between the various computer systems (0311, 0321, 0331, 0341).

A core concept in this architecture is that the PHP (0350) is configurable by healthcare providers from the hospital (0310) or other medical facility care management team members to continually drive real-time healthcare dashboard status information to authorized healthcare provider recipients based on real-time patient information collected from remote monitoring devices (RMD) communicating with mobile user devices (MUD) (0321) as well as information gathered from patient caregiver interfaces (0331) and information collected from real-time data extraction processes (0314) operating within the HIS (0311) environment. Since current healthcare methodologies isolate the HIS (0311) system within the context of a defined hospital (0310) healthcare environment, coordination of information among healthcare professionals after the patient leaves this environment has been problematic. By providing a healthcare web server (HWS) (0340) incorporating web portals accessible by the authorized healthcare providers, the system as depicted permits a unified patient healthcare plan (PHP) (0350) to act as the driver for the delivery of healthcare to the patient as well as the hub for reporting patient status to all interested and authorized healthcare professionals servicing the patient.

Within the context of the hospital setting (0310), data is continually collected by the healthcare information system (HIS) (0311) computer from a wide variety of data sources (0312) such as lab results, patient history information, chart diagnoses, procedures, surgeries, patient vital signs, etc. This information normally flows directly from the data sources (0312) to the HIS (0311) (via manual or automated input) and is collected for deposit within the patient electronic medical record (EMR) database (0313). The present invention inserts a software module (0314) (as executed machine instructions read from a computer readable medium (0315)) in this HIS (0311) context to sniff these data flows and extract information associated with various patients. This real-time patient data is then used as input to the patient healthcare plan (PHP) (0350) to drive patient care and also as input to a real-time process (0314) configured to risk stratify patients before and after they leave the hospital (0310) setting. This permits the care management team or other healthcare providers to have a real-time risk stratification dashboard (0316) that allows at-risk patients to be immediately identified for additional care or modifications to their PHP (0350). This is in contrast to prior art systems that are unable to gather patient data across various physician-care boundaries and integrate this information into a coherent risk stratification analysis.

By integrating in-patient information, out-patient information, and information gathered from various healthcare providers (0332), it is possible to immediately address declines in patient health with proactive measures rather than waiting until these conditions reach a critical stage necessitating readmission of the patient (0322) to the hospital (0310). Additionally, within the hospital (0310) context, the real-time integration of patient care information permits a real-time risk stratification dashboard (0316) to be created that allows hospital and care management staff the ability to allocate their limited resources to patients at the greatest risk of a severe medical event.

It is informative to note that less than 5% of the patient population account for 50% of the cost of patient care. Among this group, annual medical expenses equaled or exceeded USD$11487 per person. In contrast, the 50% of the population with the lowest healthcare expenses accounts for only about 3% of overall U.S. medical spending, with an annual medical spending below USD$664 per person. Thus, those in the top 5% of healthcare utilization spent on average more than 17 times as much per person as those in the bottom 50% of healthcare spenders. From this data it is clear that allocating resources optimally to at-risk patients can have a significant impact on the overall cost of healthcare within the hospital (0310) environment. The present invention in this context permits the hospital (0310) and other healthcare professionals (0332) the ability to maintain a real-time status dashboard of patient medical conditions and within this framework address at-risk patients immediately to minimize their overall cost to the healthcare delivery system.

With respect to the patient remote monitoring system (0320), the MUD (0321) operates as the main user (0322) interface, but with respect to the video data extension system embodiment described herein is augmented with a video control unit (VCU) (0323) and video display unit (VDU) (0324) that are coordinated via the use of a user interface context (UIC) control that is executed within the VCU (0323) to integrate mobile video content (MVC) provided by the overall healthcare system across the MUD (0321) and the VDU (0324). The patient healthcare plan (PHP) (0350) may be configured to dictate the operation of individual UIC modes that drive the coordinated MUD (0321) and VDU (0324) patient (0322) input/output experience.

It should be noted that in this healthcare delivery context the use of the VDU (0324) in conjunction with the MUD (0321) is significant in that many patients (0322) are elderly or visually impaired and the use of a MUD (0321) alone in this healthcare delivery application is therefore problematic. Integration of the MUD (0321) and the VDU (0324) provides for a more robust patient (0322) input/output experience that may overcome several of the disabilities associated with traditional patient care in this context.

Healthcare Method Embodiment Overview (0400)

Figure 4:
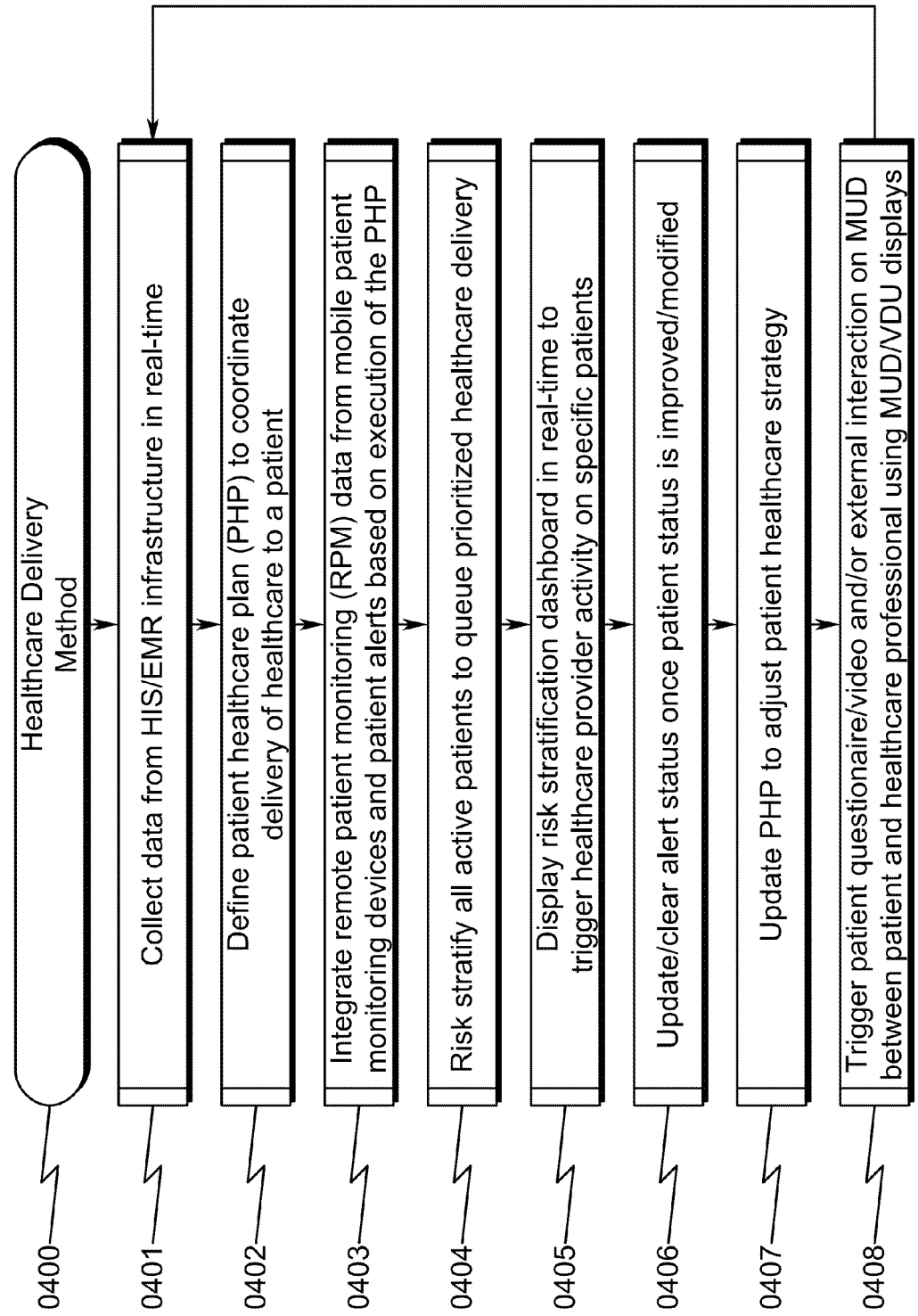
FIG. 4 illustrates a preferred exemplary overview flowchart of a preferred exemplary method embodiment of the present invention.

Associated with the exemplary system overview described in FIG. 3 (0300) is a video data extension method applied to a healthcare delivery method as depicted in FIG. 4 (0400) that comprises the following steps:

(1) Collecting patient data in real-time within a HIS/EMR infrastructure (0401);
(2) Allowing definition of a patient healthcare plan (PHP) that coordinates delivery of healthcare to a patient (0402);
(3) Integrating remote patient monitoring (RPM) data from mobile patient monitoring devices and patient alerts based on execution of the PHP (0403);
(4) Risk stratifying all active patients to queue prioritized healthcare delivery to patients (0404);
(5) Displaying risk stratification dashboards in real-time to trigger healthcare provider activity on specific patients (0405);
(6) Updating/clearing alert status once patient status is improved/modified (0406);
(7) Allowing the PHP be updated to adjust patient healthcare strategy based on patient alerts (0407); and
(8) Triggering patient questionnaires/video and/or external interaction on the MUD between the patient and healthcare professionals using a combination of the MUD and VDU as coordinated by the VCU based on alerts generated by and user interaction contexts defined by the PHP and then proceeding to step (1) (0408).

One skilled in the art will recognize that these method steps may be augmented or rearranged without limiting the teachings of the present invention. This general method summary may be augmented by the various elements described herein to produce a wide variety of invention embodiments consistent with this overall design description.

Note that in step (8) the process may rely heavily on the integration of the MUD and VDU displays in order to coordinate the deployment of the PHP to the patient in a directed or autonomous fashion. For example, the PHP may dictate a conference call with a healthcare provider that has access to the patient medical information as well as instructional videos that should be provided to the patient to improve their overall healthcare. This information may be deployed to the MUD and/or VCU for presentation to the patient in a coordinated multi-display multi-media fashion as defined by a user interaction context (UIC) described herein. This UIC may be dictated by the PHP and/or MUD to provide for a patient user experience that surpasses that which would normally be available solely from the MUD display context.

System Detail Overview (0500)

Figure 5:
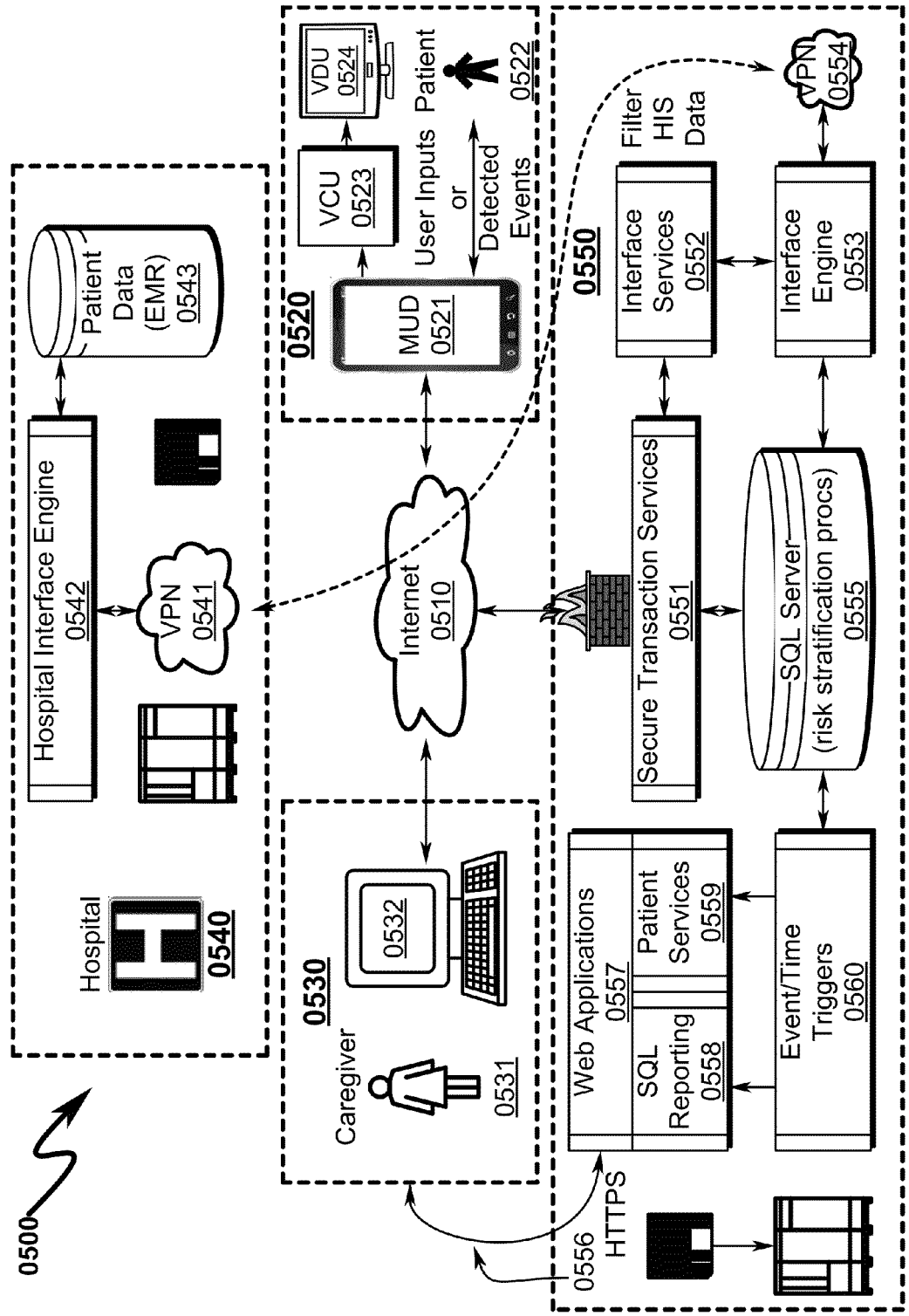
FIG. 5 illustrates a preferred exemplary data flow block diagram of a preferred exemplary system embodiment of the present invention as applied to patient healthcare delivery.

The present invention in various embodiments addresses one or more of the above objectives in the following manner as generally depicted in FIG. 5 (0500). This exemplary system embodiment is linked by a computer communications network (CCN) (0510) (typically the Internet) and consists of four separate interconnected computer systems:

Patient Portal (0520). This interface permits a patient (0522) interacting with a mobile user device (MUD) (0521) to collect medical and other information about the patient (0522) for analysis by other system components. The MUD (0521) may also be utilized in various applications to provide educational materials to the patient (0522). This presentation may occur in conjunction with a video display unit (VDU) (0524) that is controlled by a video control unit (VCU) (0523) configured to merge multi-media content from the MUD (0521) as secondary video content (SVC) and a variety of other multi-media content sourced as primary video content (PVC).

Caregiver Portal(s) (0530). This interface permits a healthcare provider (0531) (healthcare specialist, doctor, nurse, etc.) to interact with a computer system (0532) to obtain current status concerning the patient (0522) and any medical information collected by the MUD (0521). This information also permits a coordinated patient healthcare plan (PHP) to be coordinated among a number of different independently operating healthcare providers (0531).

Hospital Portal (0540). This interface permits an independently operating hospital to interact with the system via a virtual private network (VPN) (0541) to permit a hospital data interface (0542) to allow transparent access to and updating of patient healthcare data (electronic medical records) (EMR) (0543). In this manner, a hospital may integrate their existing EMR systems with healthcare providers (0531) and MUD (0521) instrumentation in a transparent manner.

Healthcare Web Server (HWS) (0550). This coordinating computer interface (also termed a healthcare computing device (HCD)) provides for a protected interface to secure transaction services (STS) (0551) that acts to coordinate data transfers between the various other system components to permit seamless integration of real-time patient medical data (0520) and healthcare plans among the healthcare providers (0530) and hospitals (0540). The STS (0551) process interacts with interface services (0552) that are specific to the various other computer systems. An interface engine (0553) is used to communicate (0554) with the MUD (0521) patient data which is then stored in a database using a SQL server (0555) (and associated data-driven risk stratification procedures). Healthcare providers (0531) interact with the HWS (0550) through a secure communication channel (0556) using one or more web applications (0557) that access SQL reporting processes (0558) or patient interface services (0559). Associated with the SQL reporting (0558) and patient services (0559) are event/time triggers (0560) that may be set by a patient healthcare plan (PHP) defined by the caregiver interface (0530) or hospital (0540). These event/time triggers (0560) are designed to inspect data collected from the patient (0522) in real-time from the MUD (0521) and trigger alerts and real-time medical status displays (0532) to healthcare providers (0531) and/or the hospital (0540) based on monitored patient healthcare data.

All of these systems (0520, 0530, 0540, 0550) are designed to operate in the context of one or more computer systems executing instructions from a computer readable medium. In the case of the HWS (0550), the secure transaction services (0551) interface and communication interfaces (0554, 0556) provide transparent interfaces to the other various computer systems through the CCN (0510). This enables existing infrastructures that deal with patient healthcare information to be updated with new patient data as it is collected from the MUD (0521) and also receive dashboard status displays and alerts from the event/time triggers (0560) concerning various patient related medical conditions. Note also that the event/time triggers (0560) may be activated by patient healthcare plan (PHP) information collected from the healthcare providers (0530) or hospitals (0540) to trigger collection of medical information from the patient, educational materials to be provided to the patient, activity to be requested from the patient, or other events that do not involve activity by the healthcare providers (0530) or hospitals (0540). This allows the PHP to independently direct patient monitoring and other activity without the need for direct healthcare provider/hospital monitoring.

One skilled in the art will recognize that the various embodiments depicted herein may be combined to produce a variety of system configurations consistent with the teachings of the invention.

Method Detail Overview (0600)

Figure 6:
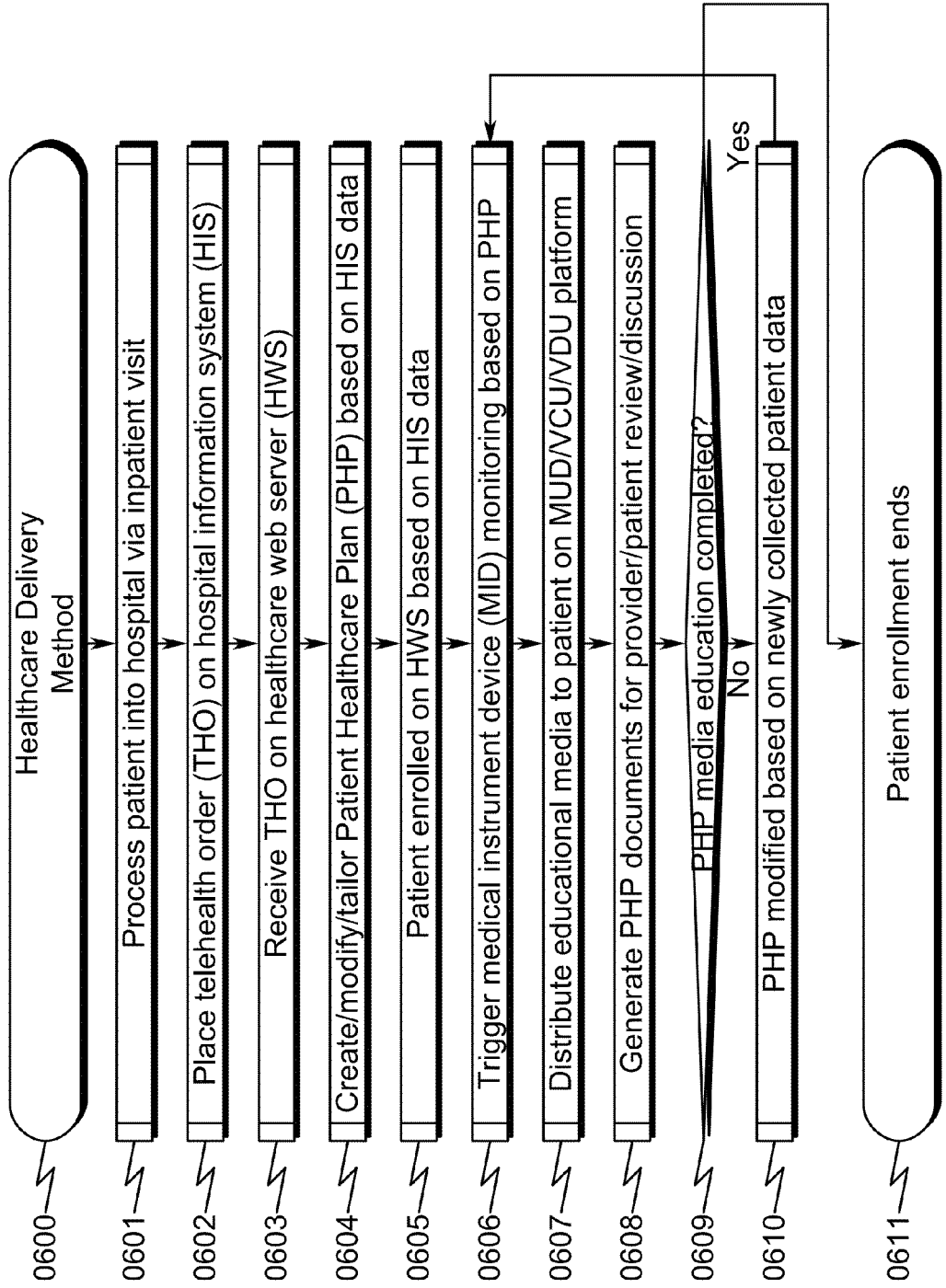
FIG. 6 illustrates a preferred exemplary flowchart of a preferred exemplary method embodiment of the present invention as applied to patient healthcare delivery.

Associated with the exemplary system overview described in FIG. 5 (0500) is a video data extension method as depicted in FIG. 6 (0600) that comprises the following steps:
(1) Processing a patient into a hospital or other healthcare service setting via an in-patient visit (0601);
(2) Placing a telehealth order (THO) on the hospital information system (HIS) for the patient (0602);
(3) Receiving the THO on a remote healthcare web server (HWS) (0603);
(4) Creating/modifying/tailoring a patient healthcare plan (PHP) on the HWS based on HIS data received in the THO (0604);
(5) Enrolling the patient on the HWS based on HIS data received (0605);
(6) Triggering medical instrument device (MID) monitoring of the patient based on the PHP (0606);
(7) Distributing medical educational media to the patient based on the PHP via a mobile user device (MUD) and under control of a user interaction context (UIC) control that is executed by a video control unit (VCU) configured to merge primary video content (PVC) from an external multi-media source and secondary video content (SVC) extracted from mobile video content (MVC) provided by a the MUD (0607);
(8) Generating PHP documents for healthcare provider/patient review and discussion (0608);
(9) Determining if PHP media education has been completed, and if so, proceeding to step (11) (0609);
(10) Modifying the PHP based on newly collected patient data and/or alerts then proceeding to step (6) (0610); and
(11) Ending the patient enrollment on the HWS (0611).

One skilled in the art will recognize that these method steps may be augmented or rearranged without limiting the teachings of the present invention. This general method summary may be augmented by the various elements described herein to produce a wide variety of invention embodiments consistent with this overall design description.

Exemplary Healthcare Delivery Information Flow (0700)

Figure 7:
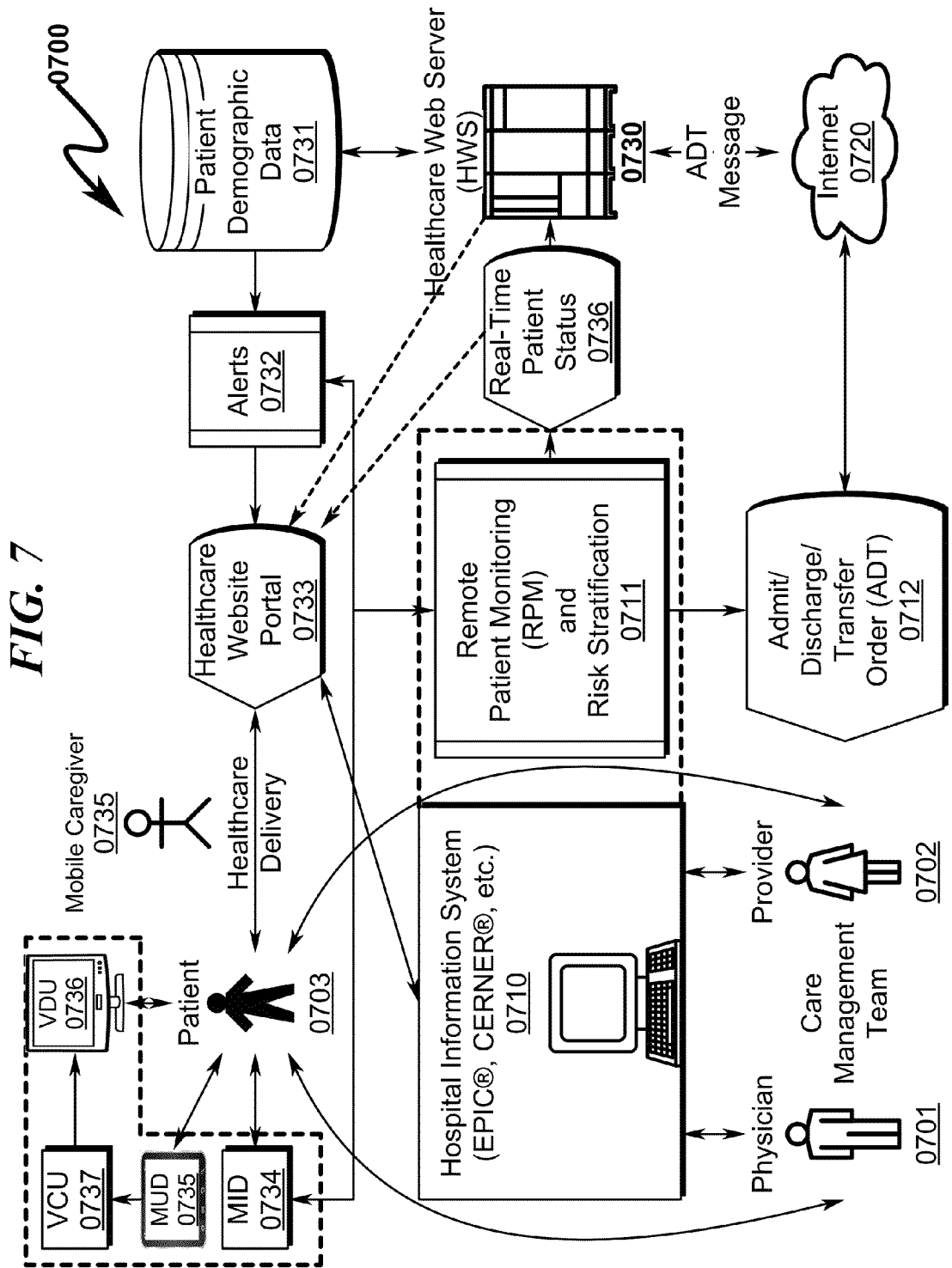
FIG. 7 illustrates a preferred exemplary data flow block diagram of a preferred exemplary system embodiment of the present invention depicting alert message integration with Hospital Information System (HIS) infrastructures and integration of MUD/VCU/VDU patient interaction displays.

Within the context of the present invention, a typical application of the video data extension system is presented as applied to healthcare delivery information flow as depicted in FIG. 7 (0700) and permits integration of in-patient/out-patient and patient alerts to be simultaneously processed with real-time multi-display content presentation to the patient. In this example, a care management team comprising a physician (0701) and/or healthcare provider (0702) interact with a hospital information system (HIS) (0710) to provide healthcare to a patient (0703). The HIS (0710) is configured with a remote patient monitoring (RPM) and risk stratification process (0711) that interfaces to data flows within the HIS (0710) and thus enable the care management team (0701, 0702) to view on dashboards a real-time status of the medical state of the patient (0703).

The care management team (0701, 0702) may generate an admit/discharge/transfer (ADT) order (0712) within the HIS and this triggers a transfer of patient information over a communication network (0720) to a healthcare web server (0730) responsible for integrating in-patient and out-patient healthcare delivery to the patient (0703). The HWS (0730) stores information related to the ADT (0712) in a patient demographic database (0731) that is then used by an alert process (0732) to generate information on a website portal (0733)

regarding potentially important patient medical information, such as that which may be collected from a medical instrument device (MID) (0734). Within this context the MID (0734) may communicate with a mobile user device (MUD) (0735) and/or a video control unit (0736) that controls the merging of audio/video information to a video display unit (VDU) (0737) such as a HDTV monitor or the like. This integration of the MUD (0735) and the VDU (0737) by the VCU (0736) permits the patient (0703) to take advantage of existing video display hardware in the home or other environment to enable video content to be presented in the most efficient manner possible. This content management (involving merging of both primary video content (PVC) and secondary video content (SVC) between the MUD (0735) and VDU (0736)) is especially important for elderly patients (0703) that have poor eyesight or diminished spatial skills.

This website portal (0733) is then accessed by an outpatient healthcare mobile caregiver (0738) to manage the care of the patient (0703) outside the context of the hospital. Note that in this context the care management team (0701, 0702) which typically operates within the context of a hospital or other healthcare facility may have identical patient views as the caregiver (0738). This permits both in-patient care and out-patient care to be coordinated among the various caregivers. Real-time patient status displays (0739) may be provided by both the HIS RPM process (0711) and accessible via the HWS (0730) website portal (0733) to enable all parties (0701, 0702, 0738) associated with the patient (0703) to be kept fully informed as to the current healthcare status of the patient (0703).

UIC Control Method (0800)

Figure 8:
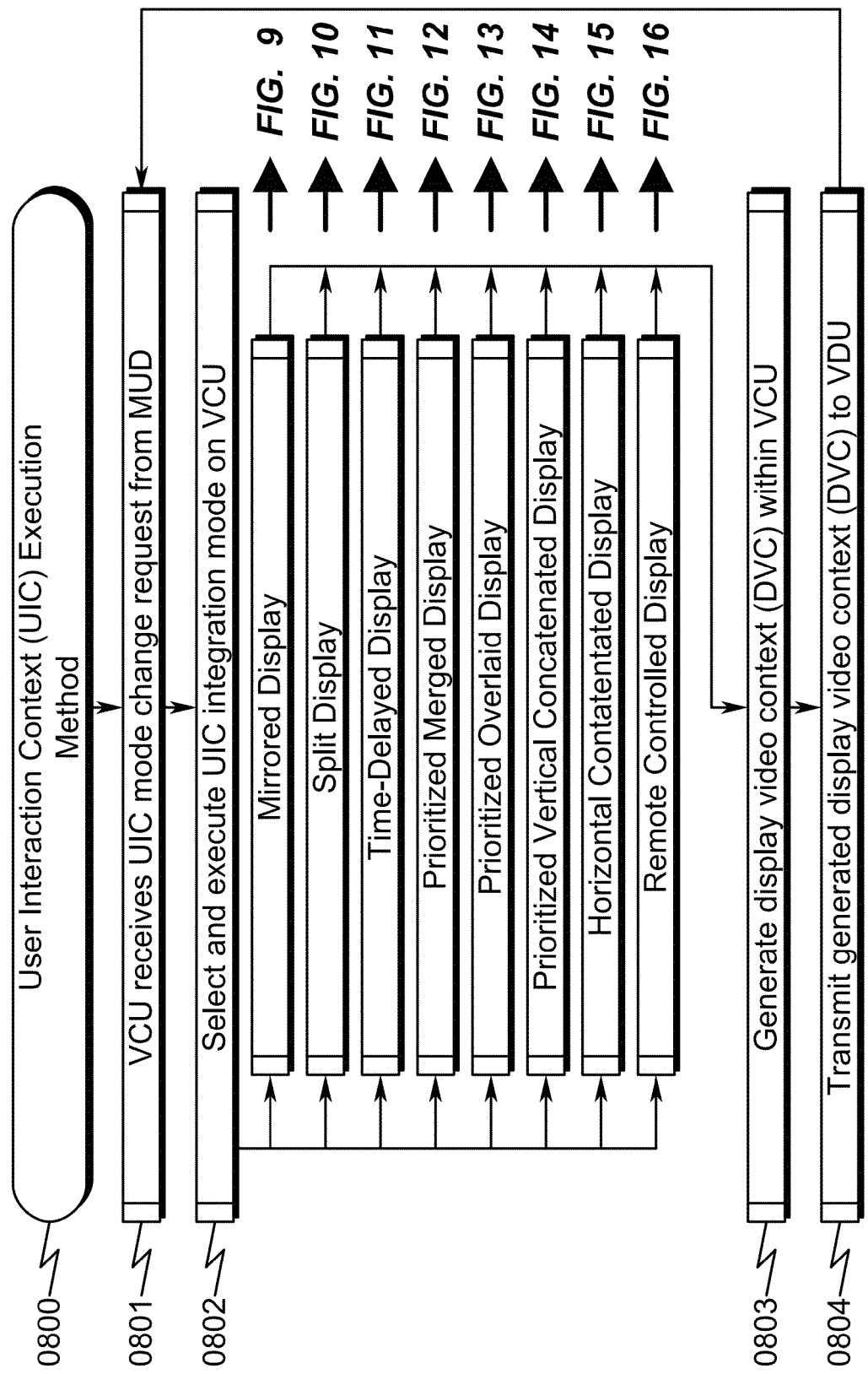
FIG. 8 illustrates a flowchart depicting an exemplary user interaction context (UIC) execution method.
Figure 9:
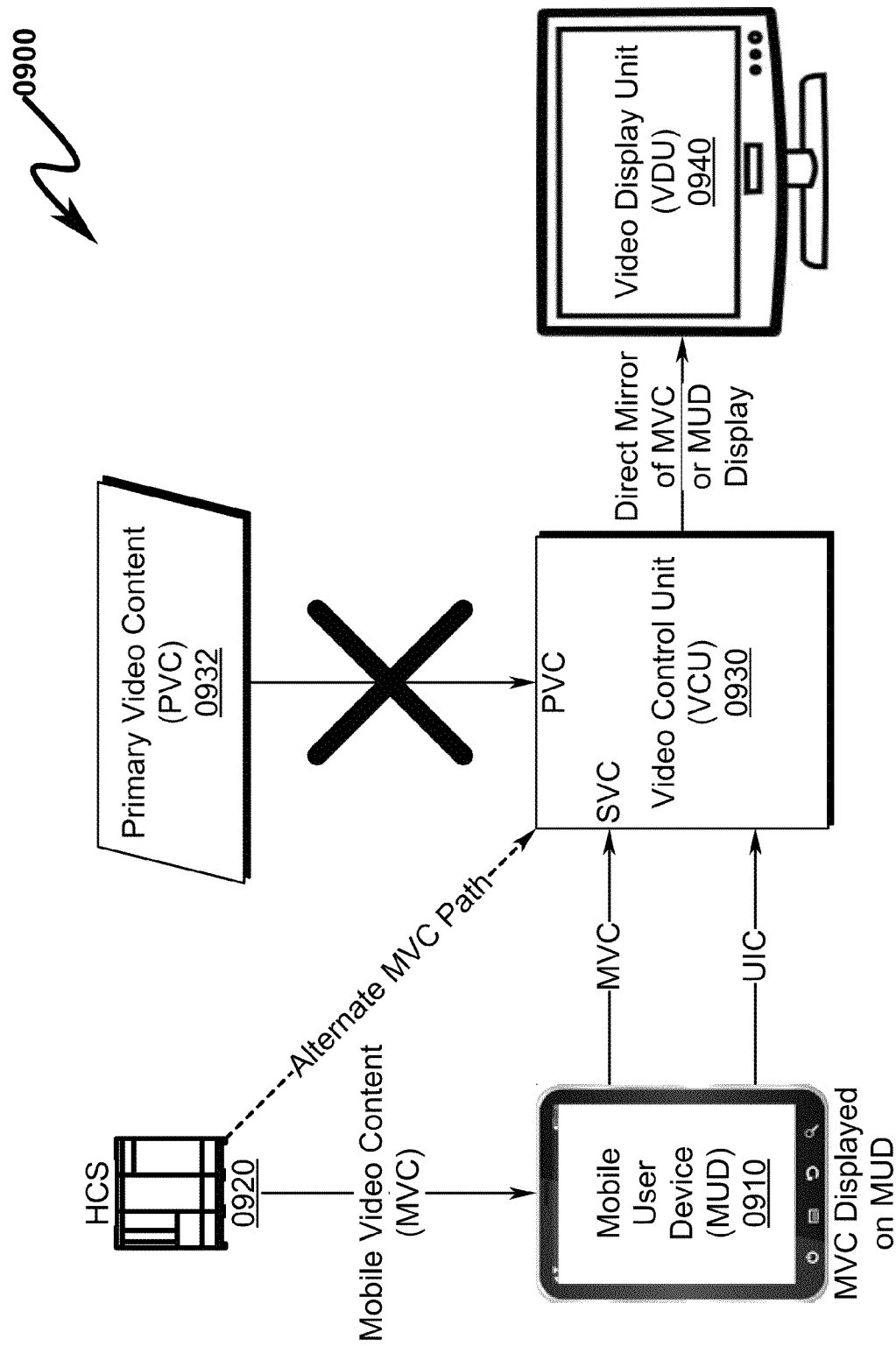
FIG. 9 illustrates an exemplary UIC depicting mirrored display of the MVC on the MUD and VDU.

Associated with the exemplary system overview described above is a UIC control method as depicted in FIG. 8 (0800) that comprises the following steps:
(1) with the VCU, receiving a UIC mode change request from the MUD (0801);
(2) selecting and executing a UIC integration mode on the VCU (0802) (exemplary UIC modes are depicted in FIG. 9 (0900)—FIG. 16 (1600) and described below);
(3) with the VCU, generating display video context (DVC) implementing the UIC mode selected (0803); and
(4) with the VCU, transmit the generated display video context (DVC) to the VDU and proceeding to step (1) (0804).
One skilled in the art will recognize that these method steps may be augmented or rearranged without limiting the teachings of the present invention. This general method summary may be augmented by the various elements described herein to produce a wide variety of invention embodiments consistent with this overall design description.

Note that the implementation of the UIC occurs in real-time and that PHP-driven patient interactions with the MUD may trigger a variety of UIC themes to be dynamically displayed on the MUD and VDU as a result of the UIC implemented by the VCU. Specific examples of exemplary UIC modes and their behavior are discussed below.

UIC Example

Mirror Display (0900)

As depicted in FIG. 9 (0900), one presently preferred user interaction context (UIC) comprises mirrored direct display of the MUD on the VDU such that the display of the MVC on the MUD is simultaneously displayed on the VDU. In this UIC, mobile video content (MVC) is distributed to the mobile user device (MUD) (0910) from the HCS (0920) via the CCN and displayed on the MUD (0910). The MVC is then communicated to the video control unit (0930) by the MUD (0910) (typically using a wireless communication network such as Wi-Fi, etc.) which then formats and displays this content as a direct mirror to generate the display video context (DVC) that is transmitted to the video display unit (0940).

In this context the VCU does not require input from the primary video content (PVC) (0932) (and this video input is disabled) as the MUD display (0910) is completely mirrored to the VDU (0940). Note that some preferred invention embodiments may configure the VCU (0930) with communication hardware and protocols that enable it to directly download the MVC from the HCS (0920) rather than obtaining this information from the MUD (0910).

UIC Example

Split Display (1000)

Figure 10:
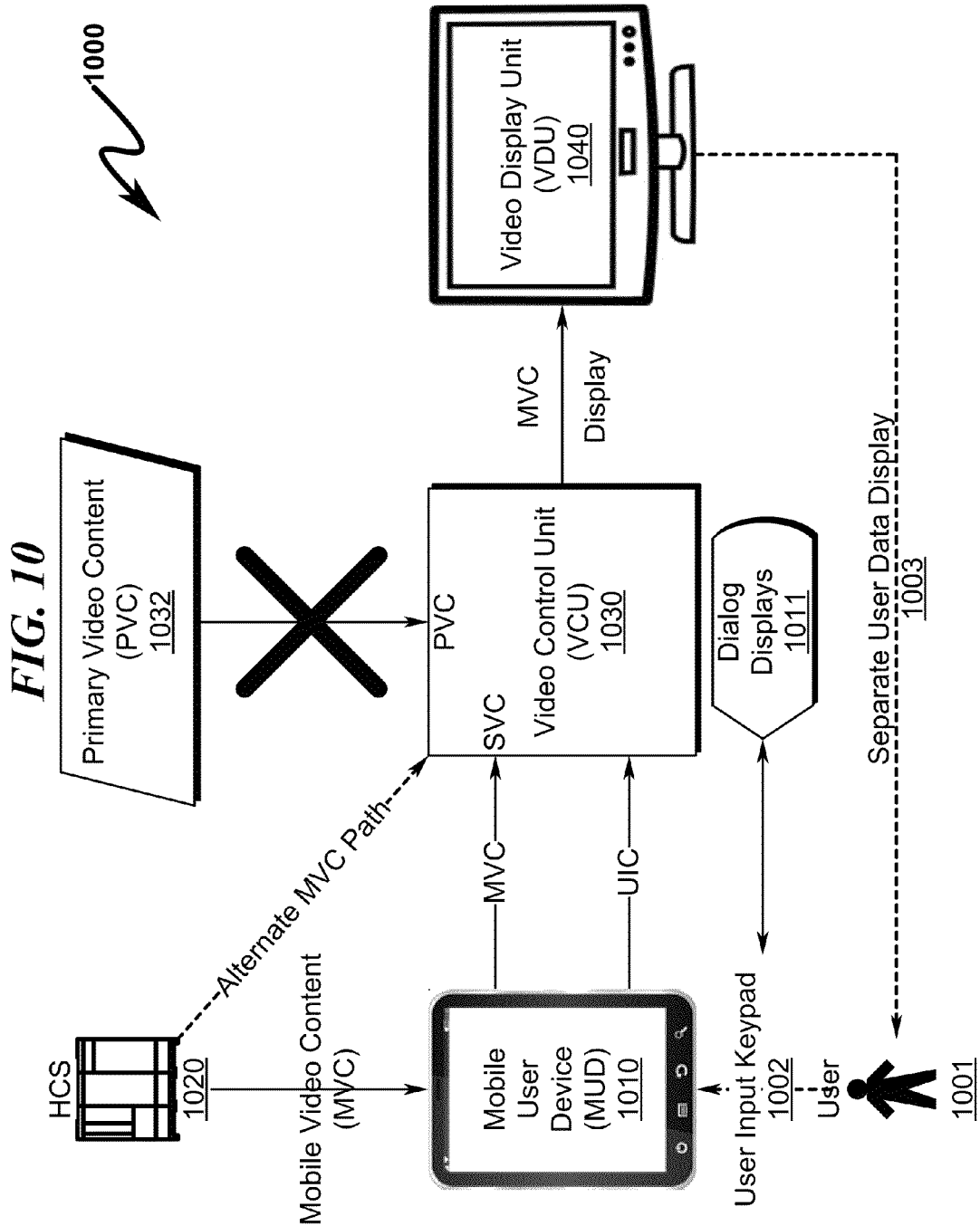
FIG. 10 illustrates an exemplary UIC depicting split input/output displays on the MUD and VDU respectively.

As depicted in FIG. 10 (1000), one presently preferred user interaction context (UIC) comprises split display of MVC input/output content on the MUD and the VDU such that the display of the MUD is associated with user input functions and the VDU is associated with user display functions. In this UIC, mobile video content (MVC) is distributed to the mobile user device (MUD) (1010) from the HCS (1020) via the CCN but not displayed on the MUD (1010). The MVC is then communicated to the video control unit (1030) by the MUD (1010) (typically using a wireless communication network such as Wi-Fi, etc.) which then formats and displays this content to generate the display video context (DVC) that is transmitted to the video display unit (1040).

In this context the VCU does not require input from the primary video content (PVC) (1032) (and this video input is disabled) as the MUD display (1010) is utilized as a user (1001) keyboard input device (1002) and the VDU (1040) is used for display output (1003). Thus, in this UIC mode, the VDU (1040) displays content associated with the MVC provided by the HCS (1020), but this content is not displayed on the MUD (1010). Associated with control function scripts provided by the HCS (1020) are user input keypad functions (1002) that are associated with user inputs (1001) to the MUD (1010) that may include query/responses or other system control functions. These input keypad functions have associated with them dialog displays (1011) that are displayed on the MUD (1010) but not displayed on the VDU (1040).

This UIC configuration permits the user (1001) to have data input (1002) associated with the MUD (1010) while simultaneously having display functions (1003) associated with the VDU (1040). This permits the VDU (1040) screen size to be leveraged for viewing and the MUD (1010) to be utilized for keyboard input.

UIC Example

Time-Delayed Display (1100)

Figure 11:
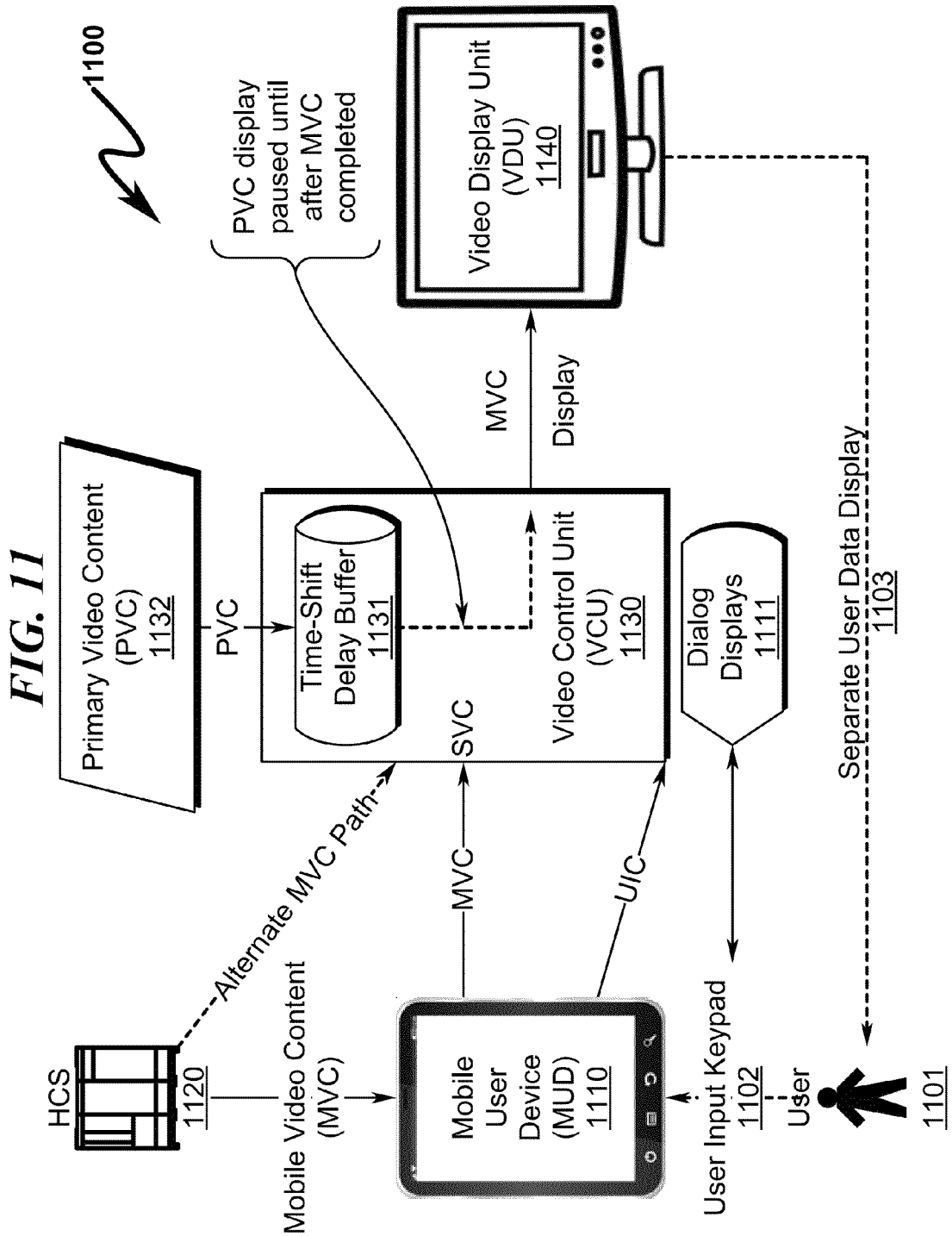
FIG. 11 illustrates an exemplary UIC depicting time-delayed (paused) display of the PVC and SVD on the VDU.

As depicted in FIG. 11 (1100), one presently preferred user interaction context (UIC) comprises time delayed merging of the PVC and the SVC on the VDU such that the SVC preempts the PVC on the VDU and while the SVC is active and the PVC is time-delayed and presented on the VDU after presentation of the SVC is completed. This UIC is similar in function to that depicted in FIG. 9 (0900) and FIG. 10 (1000) with the exception that the PVC input (1132) is not disabled during the presentation of the MVC content to the VDU (1140) and associated user (1101) input (1102) and display (1103) functions. Rather, the PVC (1132) is stored in a time-delay buffer (1131) that time-shifts (pauses) the PVC data so that it may be restarted once the user (1101) input (1102) and display (1103) functions associated with the MVC content are completed. Various preferred invention embodiments may implement this VCU PVC time-shifting function may be implemented in any number of UIC operating modes discussed herein.

UIC Example

Prioritized Merged Display (1200)

Figure 12:
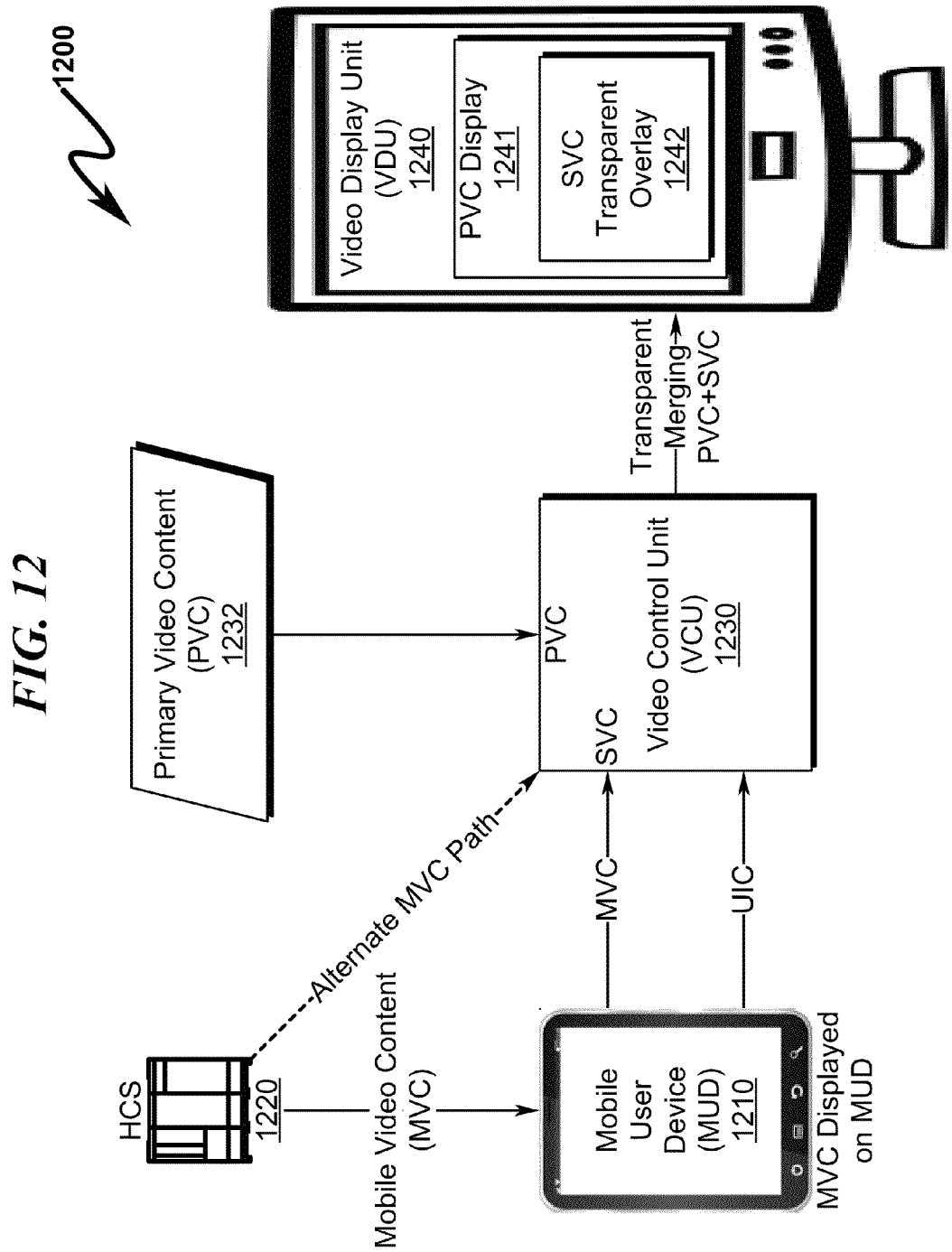
FIG. 12 illustrates an exemplary UIC depicting transparently merged displays of the PVC and SVD on the VDU.

As depicted in FIG. 12 (1200), one presently preferred user interaction context (UIC) comprises prioritized merging of the PVC and the SVC on the VDU such that the SVC transparently overlays a vertical segment of the PVC on the VDU. In this UIC, mobile video content (MVC) is distributed to the mobile user device (MUD) (1210) from the HCS (1220) via the CCN and displayed on the MUD (1210). The MVC is then communicated to the video control unit (1230) by the MUD (1210) (typically using a wireless communication network such as Wi-Fi, etc.) which then formats and transparently merges this content with the PVC (1232) to generate the display video context (DVC) that is transmitted to the video display unit (1240).

The DVC content as presented on the VDU (1240) comprises a primary PVC display (1241) that is transparently overlaid with a SVC display (1242) that comprises a portion of the vertical display (the SVC display represents a horizontal band typically located along the top or bottom of the PVC display (1241)). This permits MVC content to be displayed on the VDU (1240) without disturbing the user viewing of the PVC audio/video content. This configuration may be combined with other UIC formats (such as that depicted in FIG. 10 (1000) and FIG. 11 (1100) wherein the MUD (1210) is utilized for keypad entry and contains a display that is separate from that provided by the MVC) to provide for scenarios in which the user must respond to queries or other input functions driven by the MUD (1210).

One such scenario might occur in the execution of a patient healthcare plan (PHP) by the MUD (1240) in which timed alerts or patient queries are generated by the MUD (1240) that require responses by the patient via the MUD (1240) simulated keypad interface. In these scenarios there may be transparently overlaid alerts posted on the VDU (1240) that form a PVC (1241)/SVC (1242) merging of content on the VDU (1240).

UIC Example

Prioritized Overlaid Display (1300)

Figure 13:
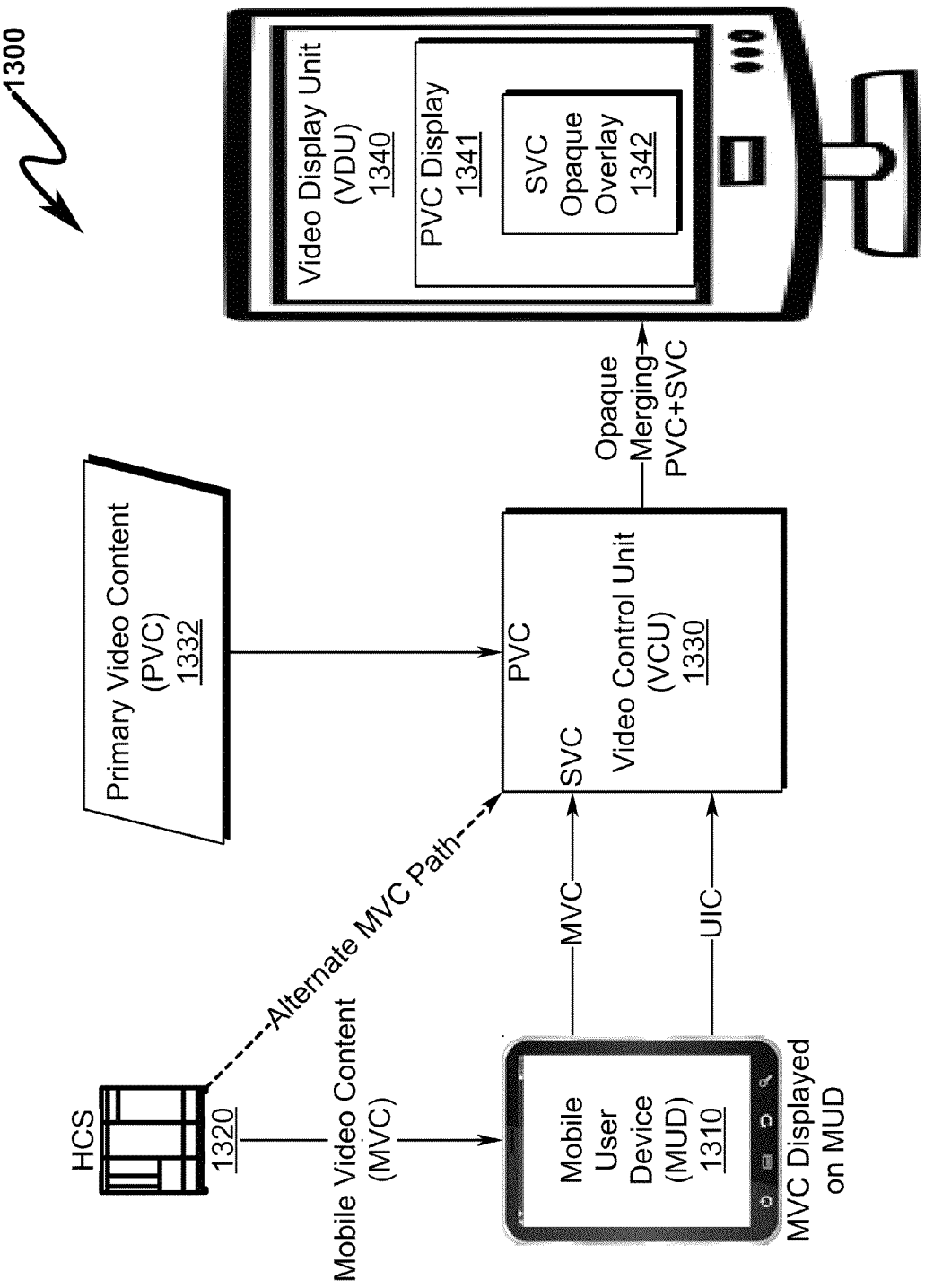
FIG. 13 illustrates an exemplary UIC depicting opaquely merged displays of the PVC and SVD on the VDU.

As depicted in FIG. 13 (1300), one presently preferred user interaction context (UIC) comprises prioritized merging of the PVC and the SVC on the VDU such that the SVC opaquely overlays a vertical segment of the PVC on the VDU. This UIC is similar to that described in FIG. 12 (1200) with the exception that the PVC display (1341) is opaquely overlaid by the SVC display (1342) on the VDU (1340).

UIC Example

Prioritized Vertical Concatenated Display (1400)

Figure 14:
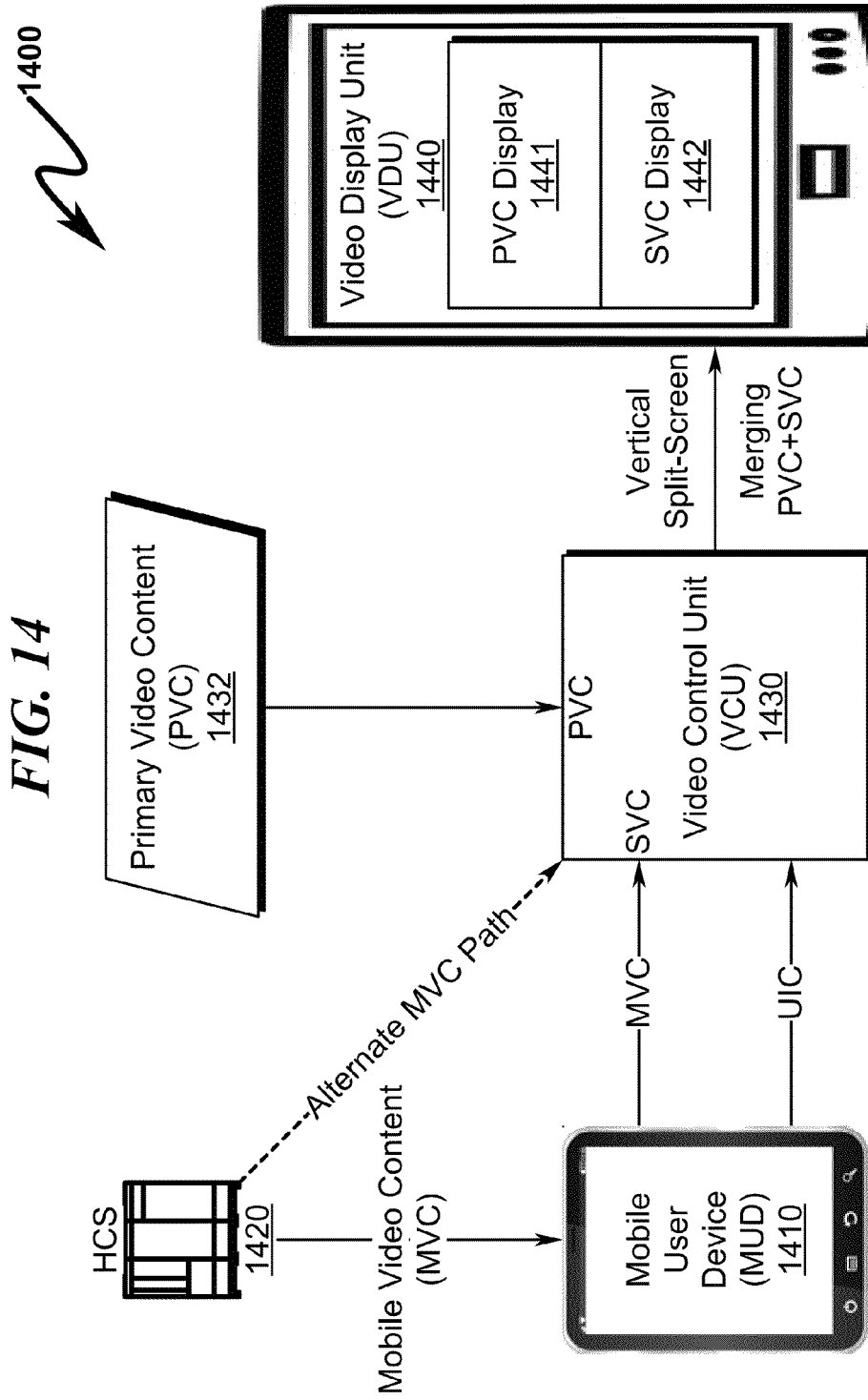
FIG. 14 illustrates an exemplary UIC depicting a prioritized vertical concatenated display comprising the MVC and PVC.

As depicted in FIG. 14 (1400), one presently preferred user interaction context (UIC) comprises prioritized vertical concatenation of the PVC and the SVC on the VDU such that the PVC and the SVC are displayed in scaled vertical split screens on the VDU. This UIC is similar to that described in FIG. 13 (1300) with the exception that the full content of both the PVC (1441) and SVC (1442) are displayed on the VDU (1440), but the content of both the PVC (1441) and SVC (1442) are vertically scaled and vertically split so as to fit on the VDU display (1440).

UIC Example

Horizontal Concatenated Display (1500)

Figure 15:
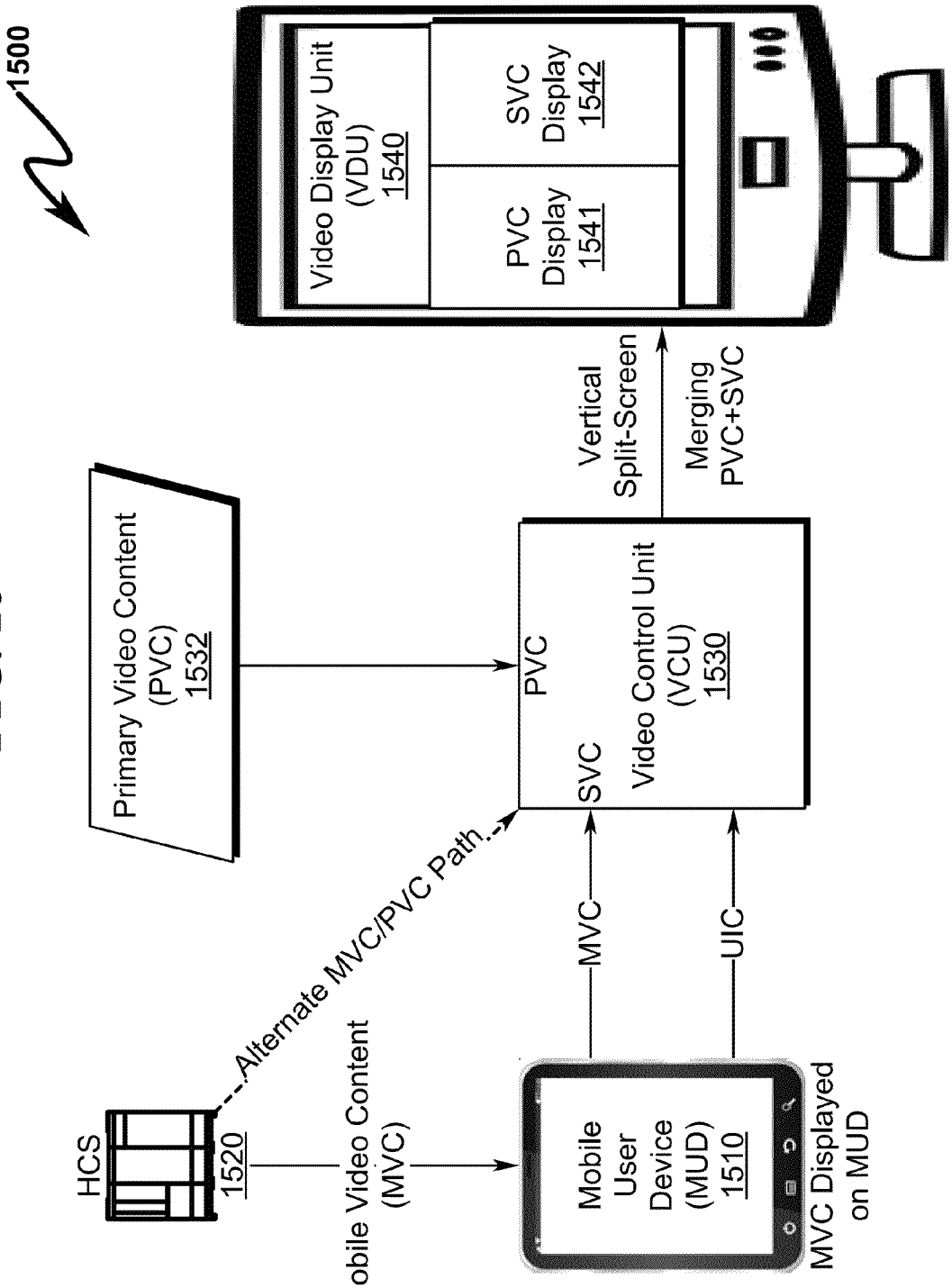
FIG. 15 illustrates an exemplary UIC depicting a horizontal concatenated display comprising the MVC and PVC.

As depicted in FIG. 15 (1500), one presently preferred user interaction context (UIC) comprises prioritized horizontal concatenation of the PVC and the SVC on the VDU such that the PVC and the SVC are displayed in scaled horizontal split screens on the VDU. This UIC is similar to that described in FIG. 14 (1400) with the exception that the full content of both the PVC (1541) and SVC (1542) are displayed on the VDU (1540), but the content of both the PVC (1541) and SVC (1542) are horizontally scaled and horizontally split so as to fit on the VDU display (1540).

In some circumstances this configuration may be used to perform split-screen communication with the VDU (1540) such that PVC (1541) display is sourced from the HCS (1520) as well as the SVC (1542) display. This may permit in some circumstances the VDU (1540) to operate in conference mode with healthcare professionals and other health caregivers to simultaneously converse with the patient while the patient views instructional video.

UIC Example

Remote Controlled Display (1600)

Figure 16:
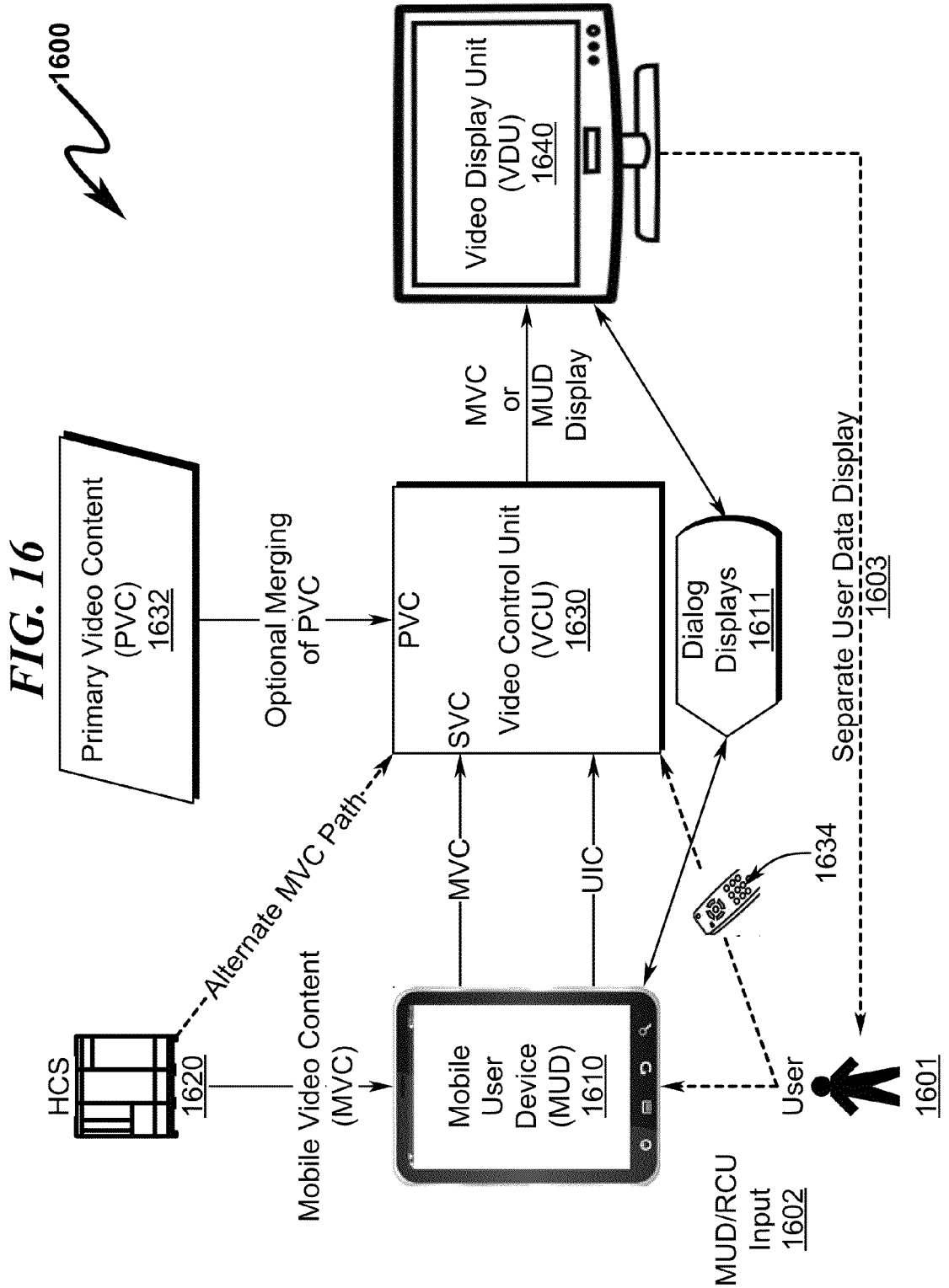
FIG. 16 illustrates an exemplary UIC depicting a remote control unit interface to the VDU.

As depicted in FIG. 16 (1600), one presently preferred user interaction context (UIC) comprises direct user interaction with the VDU using a handheld remote control unit (RCU). In this UIC, the user (1601) may interact with the VCU (1630) via a remote control unit (RCU) (1634) without the necessity for interaction with the MUD (1610). User dialog displays (1611) may be displayed simultaneously on the MUD (1610) as well as the VDU (1640) so that there is no necessity for the user (1601) to have access to the MUD (1610) to interact with the VDU (1640) content.

This scenario is useful in situations where the user (1601) is viewing PVC material using the RCU (1634) to control the VDU (1640) source content and then must make a context switch to interact with SVC material presented on the VDU (1640). By permitting interaction with the RCU (1634) in this context as the user input device (1602), the user (1601) is relieved from switching input devices if the MUD (1610) is not readily accessible. This methodology is especially useful in situations where the user (1601) must respond to queries posed by MVC material that is presented on the VDU (1640) in conjunction with PVC material, such as in the case of a MUD/MVC query that is presented during the presentation of a movie or other form of entertainment.

PHP Control of UIC Modes

The present invention anticipates that any UIC mode executed on the VCU may be triggered for activation by scripts driven by a patient healthcare plan (PHP) as defined by the HEALTHCARE DELIVERY SYSTEM AND METHOD patent application incorporated herein by reference. Thus, the MUD as described herein may communicate with the HSC to download PHP scripts that interoperate with medical instrumentation devices (MIDs) to collect patient medical data as well as prompt the user with queries and accept responses to collectively trigger alerts and data messages to remote healthcare personnel serviced by a healthcare web server (HWS) (which may comprise the HCS as described herein). Within this overall context of healthcare management, the PHP may also communicate with the VCU to trigger UIC activation on the VCU and thus coordinate the presentation of user input and output functions among the MUD and VDU to provide an integrated user input/output data collection and display experience.

Preferred Embodiment System Summary

The present invention preferred exemplary system embodiment anticipates a wide variety of variations in the basic theme of construction, but can be generalized as a video data extension system comprising:
- (a) mobile user device (MUD);
- (b) video control unit (VCU);
- (c) host computer system (HCS); and
- (d) computer communication network (CCN);

wherein
- the MUD is configured to retrieve mobile video content (MVC) from the HCS via the CCN;
- the MUD is configured to transmit the MVC to the VCU via a wireless communication link (WCL);
- the VCU is configured to accept primary video content (PVC) from an external video source (EVS);
- the VCU is configured to accept the MVC as secondary video content (SVC) from the MUD;
- the VCU is configured to merge the PVC and the SVC to generate a display video context (DVC);
- the VCU is configured to transmit the DVC to a video display unit (VDU) for presentation to a user;
- the MUD is configured to define a user interaction context (UIC) that defines the merging of the PVC and the SVC within the VCU;
- the MUD is configured to transmit the UIC to the VCU via the WCL; and
- the VCU is configured to execute the UIC to generate the DVC in real-time via the merging of the PVC and the SVC.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a video data extension method, the method operating in conjunction with a video data extension system comprising:
- (a) mobile user device (MUD);
- (b) video control unit (VCU);
- (c) host computer system (HCS); and
- (d) computer communication network (CCN);

wherein
- the MUD is configured to retrieve mobile video content (MVC) from the HCS via the CCN;
- the MUD is configured to transmit the MVC to the VCU via a wireless communication link (WCL);
- the VCU is configured to accept primary video content (PVC) from an external video source (EVS);
- the VCU is configured to accept the MVC as secondary video content (SVC) from the MUD;
- the VCU is configured to merge the PVC and the SVC to generate a display video context (DVC);
- the VCU is configured to transmit the DVC to a video display unit (VDU) for presentation to a user;
- the MUD is configured to define a user interaction context (UIC) that defines the merging of the PVC and the SVC within the VCU;
- the MUD is configured to transmit the UIC to the VCU via the WCL; and
- the VCU is configured to execute the UIC to generate the DVC in real-time via the merging of the PVC and the SVC;

wherein the method comprises the steps of:
- (1) establishing communication between the MUD and the HCS;
- (2) transferring the MVC from the HCS to the MUD;
- (3) establishing communication is established between the MUD and the VCU via the WCL;
- (4) with the MUD, selecting the UIC on the MVC;
- (5) with the MUD, transmitting the UIC along with the MVC as the SVC to the VCU using the WCL;
- (6) with the VCU, merging the PVC and SVC in real-time to form the DVC based on the UIC;
- (7) with the VCU, transmitting the DVC to the VDU; and
- (8) presenting the DVC to the user on the VDU.

One skilled in the art will recognize that these method steps may be augmented or rearranged without limiting the teachings of the present invention. This general method summary may be augmented by the various elements described herein to produce a wide variety of invention embodiments consistent with this overall design description.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:
- An embodiment wherein the CCN comprises the Internet.
- An embodiment wherein the WCL comprises a BLUETOOTH® wireless communication link.
- An embodiment wherein the UIC is defined by a patient healthcare plan (PHP) executing within the context of the MUD.
- An embodiment wherein the UIC comprises mirrored direct display of the MUD on the VDU such that the display of the MVC on the MUD is simultaneously displayed on the VDU.
- An embodiment wherein the UIC comprises split display of MVC input/output content on the MUD and the VDU such that the display of the MUD is associated with user input functions and the VDU is associated with user display functions.
- An embodiment wherein the UIC comprises time delayed merging of the PVC and the SVC on the VDU such that the SVC preempts the PVC on the VDU and while the SVC is active and the PVC is time-delayed and presented on the VDU after presentation of the SVC is completed.

An embodiment wherein the UIC comprises prioritized merging of the PVC and the SVC on the VDU such that the SVC transparently overlays a vertical segment of the PVC on the VDU.

An embodiment wherein the UIC comprises prioritized merging of the PVC and the SVC on the VDU such that the SVC opaquely overlays a vertical segment of the PVC on the VDU.

An embodiment wherein the UIC comprises prioritized vertical concatenation of the PVC and the SVC on the VDU such that the PVC and the SVC are displayed in scaled vertical split screens on the VDU.

An embodiment wherein the UIC comprises prioritized horizontal concatenation of the PVC and the SVC on the VDU such that the PVC and the SVC are displayed in scaled horizontal split screens on the VDU.

An embodiment wherein the UIC comprises direct user interaction with the VDU using a handheld remote control unit (RCU).

One skilled in the art will recognize that other embodiments are possible based on combinations of elements taught within the above invention description.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A system and method extending mobile video data across multiple display hardware platforms has been disclosed. The system incorporates a mobile user interface device (MUD) interacting with a video control unit (VCU) to present display video content (DVC) on a video display unit (VDU). The MUD and VCU coordinate to control their respective display content in real-time based on a specific integrated user interaction context (UIC) provided by the MUD to the VCU. The VCU executes the UIC to control the merging in real-time of primary video content (PVC) and secondary video content (SVC) that are combined to form the DVC. Video content processed by the VCU as PVC/SVC input may be sourced from external video sources (EVS) directly connected to the VCU and/or data sourced from a computer communications network (CCN) via routing through the MUD and/or VCU.

What is claimed is:

1. A video data extension system comprising:
    (a) mobile user device (MUD);
    (b) video control unit (VCU);
    (c) host computer system (HCS); and
    (d) computer communication network (CCN);
    wherein
    said MUD is configured to retrieve mobile video content (MVC) from said HCS via said CCN;
    said MUD is configured to transmit said MVC to said VCU via a wireless communication link (WCL) through a wireless router;
    said VCU is physically separated from said MUD;
    said VCU is configured to accept primary video content (PVC) from an external video source (EVS);
    said VCU is configured to accept said MVC as secondary video content (SVC) from said MUD;
    said VCU is configured to merge said PVC and said SVC to generate a display video context (DVC);
    said VCU is configured to transmit said DVC to a video display unit (VDU) for presentation to a user;
    said VCU is configured to execute scripts that interoperate with medical instrumentation devices (MIDs) to collect medical data from a patient as well as prompt said patient with queries and accept responses to collectively trigger alerts and data messages to remote healthcare personnel serviced by a healthcare web server (HWS);
    said VDU comprises a HDTV monitor that is physically separated from and electrically coupled to said VCU;
    said MUD is configured to define a user interaction context (UIC) that defines said merging of said PVC and said SVC within said VCU;
    said MUD is configured to transmit said UIC to said VCU via said WCL; and
    said VCU is configured to execute said UIC to generate said DVC in real-time via said merging of said PVC and said SVC.

2. The video data extension system of claim 1 wherein said UIC is triggered for activation by a patient healthcare plan (PHP) executing within the context of said MUD wherein said PHP coordinates the delivery of healthcare to a patient under autonomous control of said MUD.

3. The video data extension system of claim 1 wherein said UIC comprises mirrored direct display of said MUD on said VDU such that the display of said MVC on said MUD is simultaneously displayed on said VDU.

4. The video data extension system of claim 1 wherein said UIC comprises split display of MVC input/output content on said MUD and said VDU such that the display of said MUD is associated with user input functions and said VDU is associated with user display functions.

5. The video data extension system of claim 1 wherein said UIC comprises time delayed merging of said PVC and said SVC on said VDU such that said SVC preempts said PVC on said VDU and while said SVC is active and said PVC is time-delayed and presented on said VDU after presentation of said SVC is completed.

6. The video data extension system of claim 1 wherein said UIC comprises prioritized merging of said PVC and said SVC on said VDU such that said SVC transparently overlays a vertical segment of said PVC on said VDU.

7. The video data extension system of claim 1 wherein said UIC comprises prioritized merging of said PVC and said SVC on said VDU such that said SVC opaquely overlays a vertical segment of said PVC on said VDU.

8. The video data extension system of claim 1 wherein said UIC comprises prioritized vertical concatenation of said PVC and said SVC on said VDU such that said PVC and said SVC are displayed in scaled vertical split screens on said VDU.

9. The video data extension system of claim 1 wherein said UIC comprises prioritized horizontal concatenation of said PVC and said SVC on said VDU such that said PVC and said SVC are displayed in scaled horizontal split screens on said VDU.

10. The video data extension system of claim 1 wherein said UIC comprises direct user interaction with said VDU using a handheld remote control unit (RCU).

11. A video data extension method comprising:
(1) establishing communication between a mobile user device (MUD) and a host computer system (HCS);
(2) with said HCS, transferring mobile video content (MVC) from said HCS to said MUD via a computer communication network (CCN);
(3) with said MUD, retrieving said MVC from said HCS via said CCN;
(4) establishing communication between said MUD a video control unit (VCU) via a wireless communication link (WCL);
(5) with said MUD, transmitting said MVC to said VCU via said WCL;
(6) with said VCU, accepting primary video content (PVC) from an external video source (EVS);
(7) with said VCU, accepting said MVC as secondary video content (SVC) from said MUD;
(8) with said VCU, merging said PVC and said SVC to generate a display video context (DVC);
(9) with said VCU, transmitting said DVC to a video display unit (VDU) for presentation to a user;
(10) with said MUD, defining a user interaction context (UIC) that defines said merging of said PVC and said SVC within said VCU;
(11) with said MUD, selecting said UIC on said MVC;
(12) with said MUD, transmitting said UIC along with said MVC as said SVC to said VCU using said WCL;
(13) with said VCU, merging said PVC and SVC in real-time to form said DVC based on said UIC;
(14) with said VCU, executing said UIC to generate said DVC in real-time via said merging of said PVC and said SVC;
(15) with said VCU, executing scripts that interoperate with medical instrumentation devices (MIDs) to collect medical data from a patient as well as prompt said patient with queries and accept responses to collectively trigger alerts and data messages to remote healthcare personnel serviced by a healthcare web server (HWS);
(16) with said VCU, transmitting said DVC to said VDU; and
(17) presenting said DVC to said user on said VDU.

12. The video data extension method of claim 11 wherein said UIC is triggered for activation by a patient healthcare plan (PHP) executing within the context of said MUD wherein said PHP coordinates the delivery of healthcare to a patient under autonomous control of said MUD.

13. The video data extension method of claim 11 wherein said UIC comprises mirrored direct display of said MUD on said VDU such that the display of said MVC on said MUD is simultaneously displayed on said VDU.

14. The video data extension method of claim 11 wherein said UIC comprises split display of MVC input/output content on said MUD and said VDU such that the display of said MUD is associated with user input functions and said VDU is associated with user display functions.

15. The video data extension method of claim 11 wherein said UIC comprises time delayed merging of said PVC and said SVC on said VDU such that said SVC preempts said PVC on said VDU and while said SVC is active and said PVC is time-delayed and presented on said VDU after presentation of said SVC is completed.

16. The video data extension method of claim 11 wherein said UIC comprises prioritized merging of said PVC and said SVC on said VDU such that said SVC transparently overlays a vertical segment of said PVC on said VDU.

17. The video data extension method of claim 11 wherein said UIC comprises prioritized merging of said PVC and said SVC on said VDU such that said SVC opaquely overlays a vertical segment of said PVC on said VDU.

18. The video data extension method of claim 11 wherein said UIC comprises prioritized vertical concatenation of said PVC and said SVC on said VDU such that said PVC and said SVC are displayed in scaled vertical split screens on said VDU.

19. The video data extension method of claim 11 wherein said UIC comprises prioritized horizontal concatenation of said PVC and said SVC on said VDU such that said PVC and said SVC are displayed in scaled horizontal split screens on said VDU.

20. The video data extension method of claim 11 wherein said UIC comprises direct user interaction with said VDU using a handheld remote control unit (RCU).

21. A tangible non-transitory computer usable medium having computer-readable program code means embodied thereon comprising a video data extension method, said method comprising:
(1) establishing communication between a mobile user device (MUD) and a host computer system (HCS);
(2) with said HCS, transferring mobile video content (MVC) from said HCS to said MUD via a computer communication network (CCN);
(3) with said MUD, retrieving said MVC from said HCS via said CCN;
(4) establishing communication between said MUD a video control unit (VCU) via a wireless communication link (WCL);
(5) with said MUD, transmitting said MVC to said VCU via said WCL;
(6) with said VCU, accepting primary video content (PVC) from an external video source (EVS);
(7) with said VCU, accepting said MVC as secondary video content (SVC) from said MUD;
(8) with said VCU, merging said PVC and said SVC to generate a display video context (DVC);
(9) with said VCU, transmitting said DVC to a video display unit (VDU) for presentation to a user;
(10) with said MUD, defining a user interaction context (UIC) that defines said merging of said PVC and said SVC within said VCU;
(11) with said MUD, selecting said UIC on said MVC;
(12) with said MUD, transmitting said UIC along with said MVC as said SVC to said VCU using said WCL;
(13) with said VCU, merging said PVC and SVC in real-time to form said DVC based on said UIC;

(14) with said VCU, executing said UIC to generate said DVC in real-time via said merging of said PVC and said SVC;

(15) with said VCU, executing scripts that interoperate with medical instrumentation devices (MIDs) to collect medical data from a patient as well as prompt said patient with queries and accept responses to collectively trigger alerts and data messages to remote healthcare personnel serviced by a healthcare web server (HWS);

(16) with said VCU, transmitting said DVC to said VDU; and

(17) presenting said DVC to said user on said VDU.

22. The computer usable medium of claim 21 wherein said UIC is triggered for activation by a patient healthcare plan (PHP) executing within the context of said MUD wherein said PHP coordinates the delivery of healthcare to a patient under autonomous control of said MUD.

23. The computer usable medium of claim 21 wherein said UIC comprises mirrored direct display of said MUD on said VDU such that the display of said MVC on said MUD is simultaneously displayed on said VDU.

24. The computer usable medium of claim 21 wherein said UIC comprises split display of MVC input/output content on said MUD and said VDU such that the display of said MUD is associated with user input functions and said VDU is associated with user display functions.

25. The computer usable medium of claim 21 wherein said UIC comprises time delayed merging of said PVC and said SVC on said VDU such that said SVC preempts said PVC on said VDU and while said SVC is active and said PVC is time-delayed and presented on said VDU after presentation of said SVC is completed.

26. The computer usable medium of claim 21 wherein said UIC comprises prioritized merging of said PVC and said SVC on said VDU such that said SVC transparently overlays a vertical segment of said PVC on said VDU.

27. The computer usable medium of claim 21 wherein said UIC comprises prioritized merging of said PVC and said SVC on said VDU such that said SVC opaquely overlays a vertical segment of said PVC on said VDU.

28. The computer usable medium of claim 21 wherein said UIC comprises prioritized vertical concatenation of said PVC and said SVC on said VDU such that said PVC and said SVC are displayed in scaled vertical split screens on said VDU.

29. The computer usable medium of claim 21 wherein said UIC comprises prioritized horizontal concatenation of said PVC and said SVC on said VDU such that said PVC and said SVC are displayed in scaled horizontal split screens on said VDU.

30. The computer usable medium of claim 21 wherein said UIC comprises direct user interaction with said VDU using a handheld remote control unit (RCU).

* * * * *